US005770623A

United States Patent [19]
Kilbourn et al.

[11] Patent Number: 5,770,623
[45] Date of Patent: Jun. 23, 1998

[54] ARGINE ANTAGONISTS FOR INHIBITION OF SYSTEMIC HYPOTENSION ASSOCIATED WITH NITRIC OXIDE PRODUCTION OR ENDOTHELIAL DERIVED RELAXING FACTOR

[75] Inventors: Robert G. Kilbourn, Naperville, Ill.; Steven S. Gross; Roberto Levi, both of New York, N.Y.; Owen W. Griffith, Milwaukee, Wis.

[73] Assignees: Board of Regents, The University of Texas System, Austin, Tex.; Cornell Research Foundation, Inc., Ithaca, N.Y.

[21] Appl. No.: 561,717

[22] Filed: Nov. 22, 1995

Related U.S. Application Data

[63] Continuation of Ser. No. 838,814, Mar. 13, 1992, abandoned, which is a continuation-in-part of Ser. No. 406,909, Sep. 19, 1989, Pat. No. 5,028,627.

[51] Int. Cl.$^6$ .................................................. A61K 31/195
[52] U.S. Cl. ........................... 514/565; 514/12; 514/930; 424/85.1; 424/85.2; 424/85.5
[58] Field of Search ........................... 514/565, 12, 930; 424/85.2, 85.5, 85.1

[56] References Cited

U.S. PATENT DOCUMENTS

| | | | |
|---|---|---|---|
| 4,282,217 | 8/1981 | Baglioni et al. | 424/240 |
| 4,477,428 | 10/1984 | Silbering et al. | 424/52 |
| 4,477,429 | 10/1984 | Silbering et al. | 424/52 |
| 4,499,067 | 2/1985 | Silbering et al. | 424/542 |
| 4,789,681 | 12/1988 | Sportoletti et al. | 514/392 |
| 5,028,627 | 7/1991 | Kilbourn et al. | 514/565 |
| 5,059,712 | 10/1991 | Griffith | 562/560 |

FOREIGN PATENT DOCUMENTS

| | | |
|---|---|---|
| WO 91/04024 | 9/1990 | WIPO . |
| WO 91/84023 | 4/1991 | WIPO ......................... A61K 31/195 |
| WO 91/09574 | 7/1991 | WIPO . |

OTHER PUBLICATIONS

Sakuma, I. et al., (1988) *Proc. Natl. Acad. Sci. USA*, 85:8664–8667.
Abstract entitled "Nitric oxide damages DNA in bacteria," *Chem. and Engineering News*, Nov. 18, 1991.
Wink et al., (1991) *Science*, 254:1001–1003.
Kilbourn et al., (1984) *J. Immunology*, 133:2577–2581.
Kilbourn et al., (1990) *Biochem. and Biophys. Res. Commun.*, 172:1132–1138.
Kilbourn, R.G., et al., (1990) *Proc. Natl. Acad. Sci. USA*, 87:3629–3632.
Schmidt et al., (1992) *Science*, 255:721–723.
Turan, A. et al., (1975) *Acta Chimica Academiae Scientiarum Hungaricae, Tomas*, 85:327–332.
Iyengar, R. et al., (1987) *Proc. Natl. Acad. Sci. USA*, 84:6369–6373.
Stuehr et al., (1987) *J. Immunology*, 139:518–525.
Marletta et al., (1988) *Biochemistry*, 27:8706–8711.

Palmer, R.M.J. et al., (1988) *Nature*, 333:664–666.
Palmer, R.M.J. et al. (1988) *Biochem. Biophys. Res. Commun.*, 153:1251–1256.
Schmidt et al., (1988) *European J. Pharmacology*, 154:213–216.
Aisaka et al., (1989) *Biochem. Biophys. Res. Commun.*, 160:881–886.
Rees, D.D. et al., (1989) *Proc. Natl. Acad. Sci. USA*, 86:3375–3378.
Stuehr, D.J., et al., (1989) *J. Exp. Med.*, 169:1011–1020.
Stuehr, D.J. et al., (1989) *Biochem. Biophys. Res. Commun.*, 161:420–426.
Piguet et al., (1989) *J. Exp. Med.*, 170:655–663.
Kilbourn et al., (1990) *J. Natl. Cancer Institute*, 82:772–776.
Gross et al. (1991) *Biochem. Biophys. Res. Commun.*, 178:823–829.
Moncada et al., "Nitric Oxide: Physiology, Pathophysiology, and Pharmacology," *Pharmacological Reviews*, 43(2):109–142, 1991, published in USA.
Moncada et al., "The L-Arginine: Nitric Oxide Pathway," *Journal of Cardiovascular Pharmacology*, 17(Suppl. 3):S1–S9, 1991, published in USA.
Parratt, J.R., and Stoclet, Jean–Claude, "Possible Role of Nitic Oxide in Refactory Hypotension Associated with Sepsis and Endotoxaemia and with Multiple Organ Failure," *Applied Cardiopulmonary Pathophysiology*, 4:143–149, 1991, published in USA.
Johnston, Jeff, "Molecular Science Sets Its Sights. On Septic Shock," *The Journal of NIH Research*, 3:61–65, 1991, published in USA.
Moncada, S., and Higgs, E.A., "Endogenous Nitric Oxide: Physiology, Pathology and Clinical Relevance," *European Journal of Clinical Investigation*, 21:361–374, 1991, published in Europe.
Palmer et al., "Nitric Oxide Release Accounts for the Biological Activity of Endothelium–Derived Relaxing Factor," *Nature*, 327:524–526, 1987, published in the United Kingdom.

(List continued on next page.)

*Primary Examiner*—Chhaya D. Sayala
*Attorney, Agent, or Firm*—Arnold, White & Durkee

[57] ABSTRACT

A method for prophylaxis or treatment of an animal for systemic hypotension induced by internal nitrogen oxide production. The method involves administering a therapeutically effective amount of certain arginine derivatives to inhibit nitrogen oxide formation from arginine. Preferably $N^G$-substituted arginine or an $N^G,N^G$-disubstituted arginine (having at least one hydrogen on a terminal guanidino amino group replaced by another atomic species) is administered to an animal possibly developing or already having such induced systemic hypotension. The arginine derivatives are preferably of the L configuration and include pharmaceutically acceptable addition salts. Prophylaxis or treatment of systemic hypotension in a patient which has been induced by chemotherapeutic treatment with biologic response modifiers such as tumor necrosis factor or interleukin-2 may be accomplished. Treatment of an animal for systemic hypotension induced by endotoxin, i.e., septic shock may also be accomplished by treatment with the arginine derivatives.

25 Claims, 22 Drawing Sheets

OTHER PUBLICATIONS

Martin et al., "Selective Blockade of Endothelium–Dependent and Glyceryl Trinitrate–Induced Relaxation by Hemoglobin and by Methylene Blue in the Rabbit Aorta," *The Journal of Pharmacology and Experimental Therapeutics*, 232(3):708–716, 1985, published in USA.

Buga et al., "Endothelium–Derived Nitric Oxide Relaxes Nonvascular Smooth Muscle," *European Journal of Pharmacology*, 161:61–72, 1989, published in Europe.

Torti et al., "A Macrophage Factor Inhibits Adipocyte Gene Expression: An in Vitro Model of Cachexia," *Science*, 229:867–871, 1985, published in USA.

Vallance et al., "Effects of Endothelium–Derived Nitric Oxide on Peripheral Arteriolar Tone in Man," *The Lancet, Ltd.*, 997–999, Oct., 1989, published in Europe.

Old, Loyd J., "Tumor Necrosis Factor (TNF)," *Science*, 23:630–632, 1985, published in USA.

Yoshida and Kasama, "Biotransformation of Nitric Oxide," *Environmental Health Perspectives*, 78:201–206, 1987, published in USA.

Reif and Simmons, "Nitric Oxide Mediates Iron Release from Ferritin," *Archives of Biochemistry and Biophysics*, 283(2):537–541, 1990, published in USA.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics*, 241(1):307–313, 1987, published in USA.

Kosaka et al., "The Interaction Between Nitrogen Oxides and Hemoglobin and Endothelium–Derived Relaxing Factor," *Free Radical Biology and Medicine*, 7:653–658, published in USA.

Chevion et al., "Iron–Nitrosyl Bond configuration in Nitrosyl–Hemoproteins: A Comparative EPR Study of Hemoglobin A and Hemoglobin Kansas," *Israel Journal of Chemistry*, 15:311–317, 1976, published in Isreal.

Collier and Vallance, "Second Messenger Role for NO Widens to Nervous and Immune Systems," *Trends in Pharmacological Sciences Including Toxicological Sciences*, Elseview Science Publishers, Ltd., front page and pp. 428–431, 1989, published in United Kingdom.

Ignarro et al., "Endothelium–Derived Relaxing Factor Produced and Released from Artery and Vein is Nitric Oxide," *Proc. Natl. Acad. Sci. USA*, 84:9265–9262, 1987, published in USA.

Murray et al., "Stabilization and Partial Characterization of Endothelium–Derived Relaxing Factor from Cultured Bovine Aortic Endothelial Cells," *Biochemical and Biophysical Research Communications*, 141(2):689–696, 1986, published in USA.

Marletta, Michael A., "Nitric Oxide: Biosynthesis and Biological Significance," name of publication unknown, Elseview Science Publishers, Ltd., pp. 448–493, 1989, published in United Kingdom.

Gruetter et al., "Coronary Arterial Relaxation and Guanylate cyclase Activation by Cigarette Smoke, N'Nitrosonornicotine and Nitric Oxide," *Journal of Pharmacology and Experimental Therapeutics*, 214(1):9–15, 1980, published in USA.

Aisaka et al., "L–$N^G$–Methylarginine, An Inhibitor of Endothelium–Derived Nitric Oxide Synthesis, Inhibits Acetylcholine–Induced Vasodilatation in the Guinea Pig," *Nitric Oxide from L–Arginine, A Bioregulatory System*, The Royal Society London, 14th/15th Sep. 1989.

Kilbourn and Belloni, "Endothelial Cells Produce Nitric Oxide in Response to Gamma Interferon and Tumor Necrosis Factor," *Nitric Oxide from L–Arginine, A Bioregulatory System*, The Royal Society London, 14th/15th Sep. 1989.

Lodato, "Decreased $O_2$ Consumption and Cardiac Output During Normobaric Hyperoxia in Conscious Dogs," American Physiological Society, p. 1551, Copyright 1989.

Sakuma et al., "L–Arginine is a Precursor of Endothelium–Derived Relazxing Factor in Various Species and Vascular Beds," *Nitric Oxide from L–Arginine, A Bioregulatory System*, The Royal Society London, 14th/15th Sep. 1989.

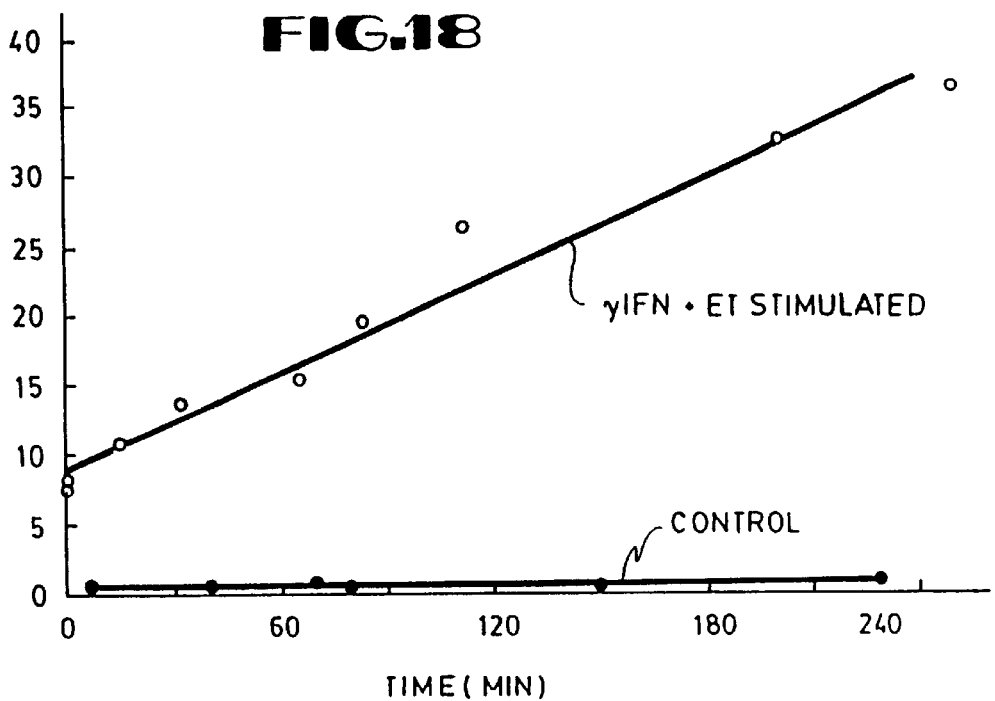
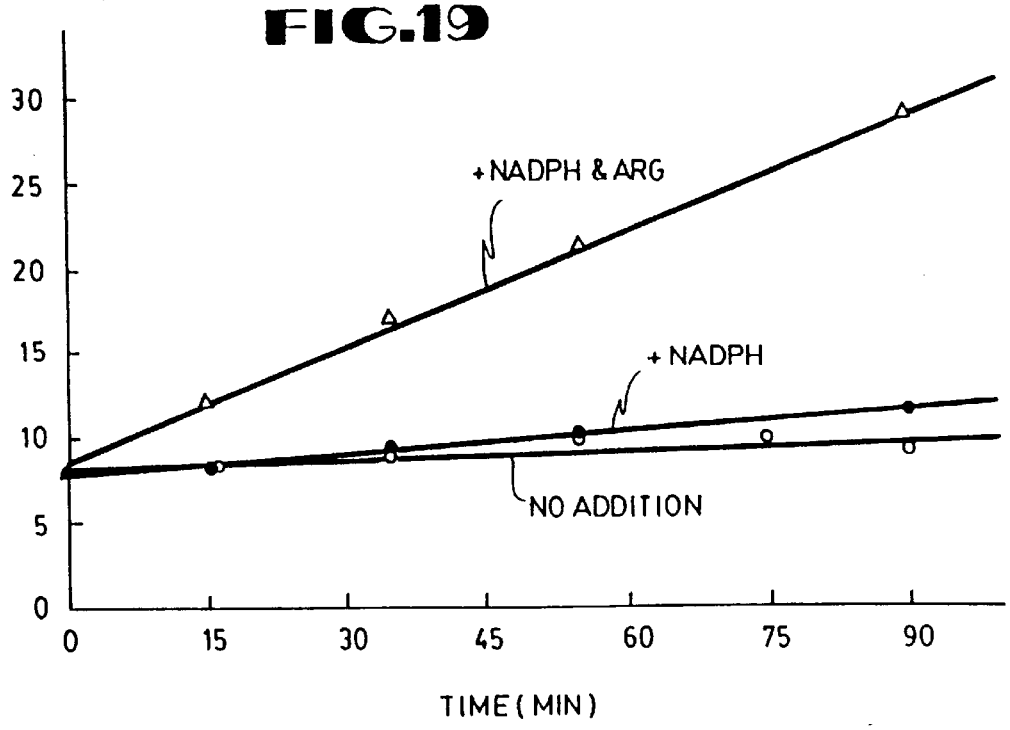

ARGINE ANTAGONISTS FOR INHIBITION OF SYSTEMIC HYPOTENSION ASSOCIATED WITH NITRIC OXIDE PRODUCTION OR ENDOTHELIAL DERIVED RELAXING FACTOR

This is a continuation of U.S. application Ser. No. 07/838,814, ABN, which was a United States national stage application 35 U.S.C. § 371 of PCT/US90/05199, filed Sep. 13, 1990, and is a continuation-in-part of U.S. Ser. No. 07/406,909 filed Sep. 13, 1989, now U.S. Pat. No. 5,028,627, issued Jul. 2, 1991.

Certain research relating to the development of this invention was supported by the United States Public Health Service grants which may give the United States government certain rights in the present invention.

The present invention relates to the prophylaxis and alleviation of hypotension induced by nitrogen oxide production.

In 1980, Furchgott and Zawadski (Nature 288: 373–376) demonstrated that endothelial cells, which line blood vessels, can be stimulated to release a substance which relaxes vascular smooth muscle i.e., causes vasodilatation. Since the chemical nature of this substance was completely unknown, it was simply named endothelium-derived relaxing factor (EDRF). It is now widely accepted that many naturally-occurring substances which act as physiological vasodilators mediate all or part of their action by stimulating release of EDRF; these substances include, acetylcholine, histamine, bradykinin, leukotrienes, ADP, ATF, substance P, serotonin, thrombin and others. Although the extremely short lifetime of EDRF (several seconds) hampered efforts to chemically identify this molecule, in 1987 several laboratories suggested that EDRF may be nitric oxide (NO), which spontaneously decomposes to nitrate and nitrite. A fundamental problem in accepting this NO hypothesis was that mammalian systems were not known to contain an enzymatic pathway which could synthesize NO; additionally, a likely precursor for NO biosynthesis was unknown. After observing that the arginine analog L-$N_G$-methylarginine (L-NMA) could inhibit vascular EDRF/NO synthesis induced by acetylcholine and histamine, and that EDRF/NO synthesis could be restored by adding excess L-arginine, certain of the present inventors proposed that arginine is the physiological precursor of EDRF/NO biosynthesis (Sakuma et al., PNAS 85: 8664–8667, 1988). Additional evidence supporting this proposal was reported almost simultaneously. Certain of the present inventors later demonstrated that inhibition of EDRF/NO synthesis in the anesthetized guinea pig raises blood pressure, suggesting that EDRF/NO is an important physiological regulator of blood pressure (Aisaka et al., BBRC 16: 881–886, 1989). Notwithstanding the accumulated evidence supporting synthesis of NO, it is understood by those skilled in the art that other nitrogen oxides may be present and may be active in reducing blood pressure. Within this specification, the acronym NO will be understood to represent nitric oxide and any additional vasoactive nitrogen oxides.

Other laboratories had demonstrated that macrophage cells become "activated" by 12–36 hour treatment with gamma-interferon, bacterial endotoxin and various cytokines. This "activation" is associated with initiation of tumor cell killing and generation of nitrite and nitrate from L-arginine. It was observed that activated macrophages actually make NO from L-arginine (just like endothelial cells) and that this NO subsequently reacts with oxygen to form more oxidized nitrogen metabolites which appear to be physiologically inert (Stuehr et al., J. Exp. Med. 169: 1011–1020, 1989). The enzyme responsible for No synthesis (nitric oxide synthetase) has been partially characterized by some of the present inventors (Stuehr et al. BBRC 161: 420–426, 1989) and acts to oxidize the terminal amino group of arginine, resulting in production of NO and citrulline. It is now believed that macrophage-derived NO is an important tumoricidal and bactericidal agent. Since bacterial endotoxin, gamma-interferon and other cytokines can trigger NO generation by macrophage cells it appeared that: 1) endothelial cell NO generation may be stimulated by similar stimuli and 2) septic shock (i.e., systemic vasodilatation induced by bacterial endotoxin) may result from massive activation of NO biosynthesis. Speculation that the latter hypothesis was correct was fueled by a prior report that urinary nitrate levels are grossly elevated by treatment of rats with bacterial endotoxin (Wagner et al., PNAS 80: 4518–4521, 1983).

Cytokines are well known to cause morphological and functional alterations in endothelial cells described as "endothelial cell activation". Distinct immune-mediators such as tumor necrosis factor (TNF), interleukin-1 (IL1), and gamma-interferon (IFN or I) appear to induce different but partially overlapping patterns of endothelial cell activation including increased procoagulant activity (Bevilaqua, 1986), PGI2 production (Rossi, 1985 Science 229,174), HLA antigen expression (Pober 1987) and lymphocyte adhesion molecules (Harlan 1985; Cavender 1987). Although these cytokines are reported to cause hypotension, vascular hemorrhage, and ischemia, the underlying mechanisms of altered vasoactivity are unclear (Goldblum et al. 1989; Tracey et al. Science 234:470, 1986). A potential mediator of altered vasoactivity is EDRF.

In both clinical and animal (Dvorak, 1959) studies on the effects of biological response modifiers a major dose limiting toxicity has been hypotension and vascular leakage.

The present invention involves a method for prophylaxis or treatment of an animal for systemic hypotension induced by a biological response modifier such as cytokines, IFN, TNF, IL-1 and IL-2. Said method involves administering, preferably intravascularly, a therapeutically effective amount of an inhibitor of nitric oxide formation from arginine. Although preferable administration is intravascular, it is contemplated that other parenteral administration routes such as intraperitoneal, intramuscular or subdermal injection, for example, may prove useful. Enteral or topical administration may also prove beneficial for certain clinical conditions.

In one embodiment the inhibitor is $N^G$-substituted arginine or an $N^G,N^G$-disubstituted arginine which is administered to an animal which is possibly developing or experiencing No-induced systemic hypotension. The arginine antagonists of the present invention are preferably of the L configuration and include any pharmaceutically acceptable addition salts as commensurate with planned treatments.

A particular use of the method of the present invention is for prophylaxis or treatment of systemic hypotension induced in a patient by chemotherapeutic treatment with tumor necrosis factor or interleukin-2 or both. In this aspect, the method involves intravascularly administering to the chemotherapy patient a therapeutically effective amount of $N^G$-substituted arginine or an $N^G,N^G$-disubstituted arginine.

An important aspect of the present invention is as a method for treatment of an animal for systemic hypotension induced by endotoxin, i.e., septic shock. Although prophylaxis is inappropriate here, treatment is essential, the treatment involving intravascularly administering to such a hypotensive animal a therapeutically effective amount of an arginine antagonist such as $N^G$-substituted arginine, $N^G,N^G$-disubstituted arginine, $N^G$-aminoarginine or $N^G$-nitroarginine.

Septic shock is a life-threatening condition that results from exposure to bacterial endotoxin. It is manifested by cardiovascular collapse and mediated by the release of cytokines such as tumor necrosis factor. Some of these cytokines cause the release of vasoactive substances. In the present study, administration of 40 μg/kg of bacterial endotoxin to dogs caused a 33% decrease in peripheral vascular resistance and a 54% fall in mean arterial blood pressure within 30 to 90 minutes. Vascular resistance and systemic arterial pressure were normalized within 1.5 minutes after intravenous administration of $N^G$-methyl-L-arginine (20 mg/kg), a potent and selective inhibitor of nitric oxide synthesis. Although $N^G$-methyl-L-arginine injection increased blood pressure in control dogs, the hypertensive effect was much greater in endotoxemic dogs (24.8±4.7 mmHg vs 47.8±6.8 mmHg, n=4). $N^G$-methyl-L-arginine caused only a modest increase in blood pressure in dogs made hypotensive by continuous intravenous infusion of nitroglycerin (17.1±5.0 mmHg, n=3.) These findings suggest that nitric oxide overproduction is an important contributor to endotoxic shock. Moreover, our findings demonstrate for the first time, the utility of nitric oxide synthesis inhibitors in endotoxic shock and suggest that such inhibitors may be of therapeutic value in the treatment of septic shock.

Preferred $N^G$-substituted arginine antagonists of the L configuration for uses as described herein include $N^G$-aminoarginine, $N^G$-nitroarginine, and $N^G$alkyl arginines such as $N^G$-methylarginine, $N^G$-ethylarginine, $N^G$-propylarginine or $N^G$-butylarginine. Therapeutically effective amounts of the substituted or disubstituted arginine antagonists inhibit production in the animal or patient of nitric oxide from arginine, thus obviating its hypotensive effects.

In a more general sense, the present invention may relate to a method for prophylaxis or treatment of an animal for systemic hypotension related to induced production of nitric oxide. Said method would involve intravascularly administering to an animal a therapeutically effective amount of an arginine antagonist for inhibiting production of nitric oxide from arginine. Effective arginine antagonists may include a wide variety of compounds, particularly arginine derivatives which inhibit nitric oxide production. Many substituents, for example, on the guanidino group of arginine or analogous citrulline functional groups should serve as well. Synthesis of hypotension-producing nitric oxide may be directly or indirectly induced by at least one of IFN, TNF, IL-1, IL-2 and endotoxin. In a preferred aspect, the arginine antagonists usable as described herein include $N^G$-substituted arginine or $N^G,N^G$-disubstituted arginine. In one embodiment, these antagonists preferably have alkyl substituents selected from the group consisting of methyl, ethyl, propyl and butyl. Analogous antagonists may include derivatized alkyl substituents selected from the group consisting of hydroxyalkyl, carboxyalkyl and aminoalkyl. The arginine antagonists usable in the practice of the present invention comprise arginine with at least one $N^G$ substituent selected from the group consisting of alkyl, hydroxyalkyl, and alkenyl. The therapeutically effective amount of arginine antagonists of the present invention is an amount sufficient to inhibit production of nitric oxide from arginine. Nitric oxide rapidly degrades to nitrate and (primarily) nitrite ions (in a fixed ratio) in the presence of oxygen; therefore, nitrites are measured clinically to indicate nitric oxide production.

When intravascularly administering to a dog a therapeutically effective amount of NKA or $N^G$-methylarginine (same as $N^G$-monomethyl L-arginine or NMMA), the therapeutically effective amount is between about 4 mg/kg and about 100 mg/kg. The appropriate dose for a human of NMMA and/or other arginine antagonists should be between about 0.1 mg/kg and about 100 mg/kg.

Abbreviations used in the drawings and other places in this application include the following. Others are defined in the text.

ACh=acetylcholine
CO=Cardiac output
EDRF=Endothelium-Derived Relaxing Factor
ET=endotoxin
GP=guinea pig
HIST=histamine
IFN=I=gamma-interferon
IV=Intravenous
L-Arg=L-arginine
L-NMA (or NMMA)=$N^G$-methyl-L-arginine=$N^G$-monomethyl-L-arginine
LPS=endotoxin in phosphate buffered saline
$LTD_4$=leukotriene $D_4$
MBEC=murine brain endothelial cells
MDP=muramyl dipeptide
NE=norepinephrine
NMA=L-NMA =NMMA=$N^G$-monomethyl-L-arginine
NO=Nitric Oxide
PAF=Platelet Activating Factor
SAP=Systemic arterial pressure
SNP=sodium nitroprusside
SVR=Systemic vascular resistance
TNF=Tumor Necrosis Factor FIG. 1 shows the effects of IFN in combination with various cytokines on the production of nitrites by brain endothelial cells (MBEC).

Figure 7:
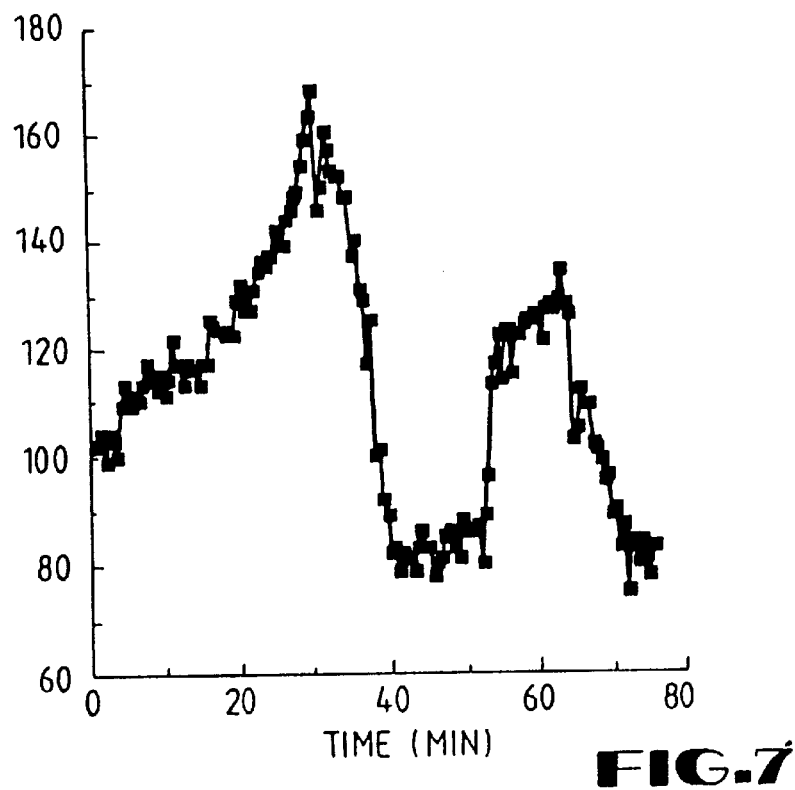
FIG. 7 illustrates variations in canine systemic blood pressure (BP) and heart rate (HR) as a function of time after sequential administration of TNF, NMMA, and L-arginine.
Figure 7A:
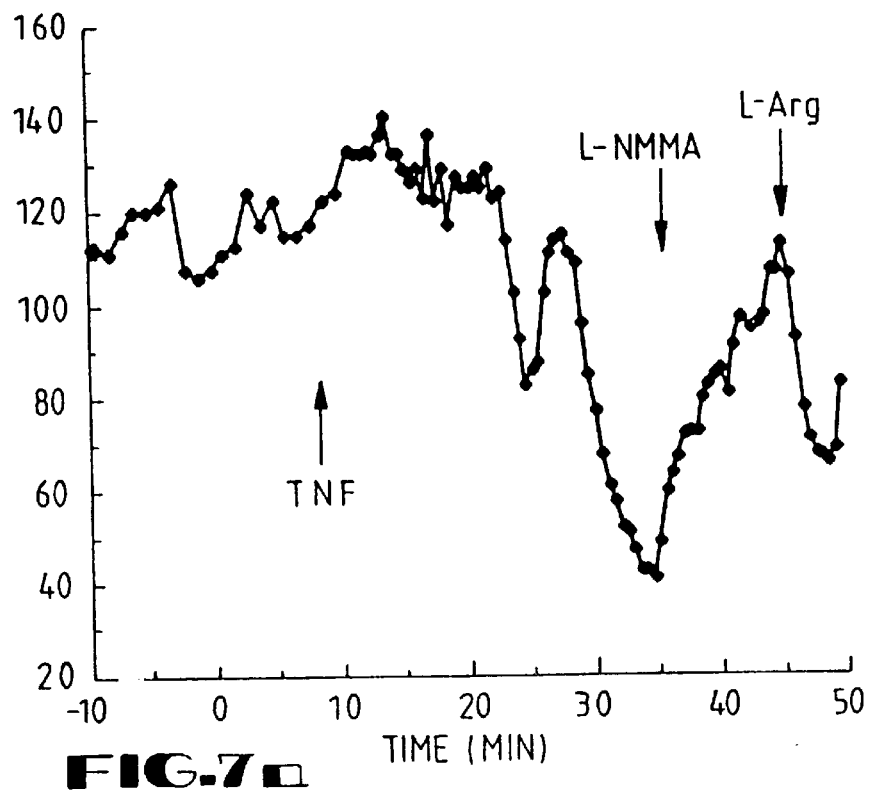

FIG. 7a also illustrates variations in canine systemic BP and HR as a function of time after sequential administration of TNF, NMMA, and L-arginine.

Figure 7B:
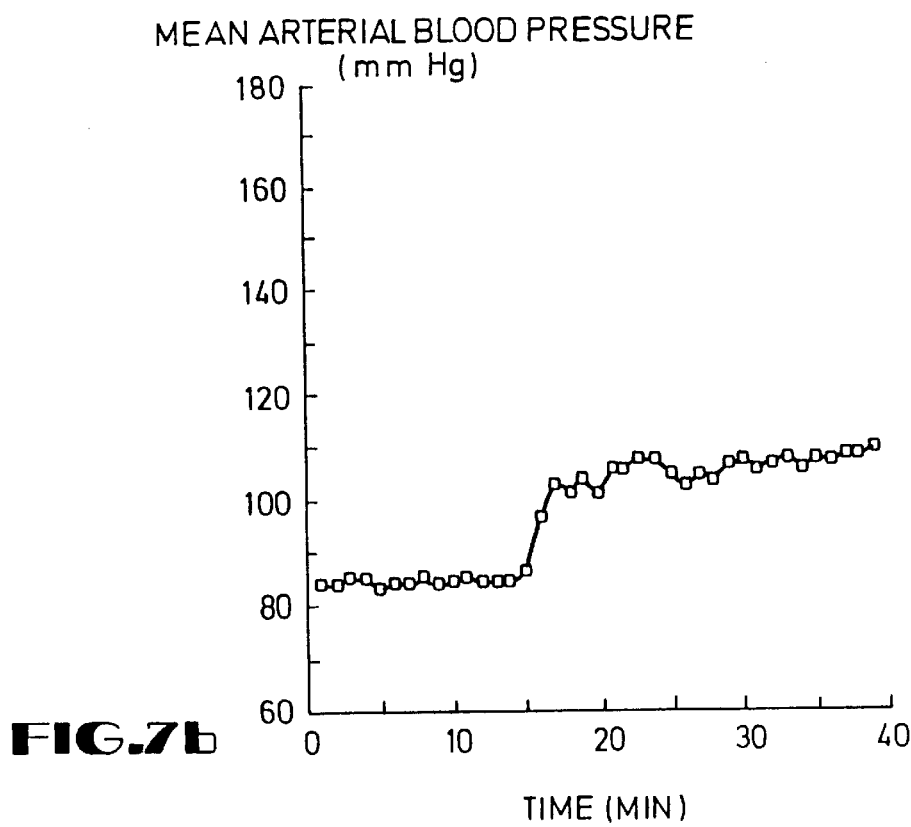

FIG. 7b illustrates control experiments where NMMA was administered to previously untreated dogs.

Figure 7C:
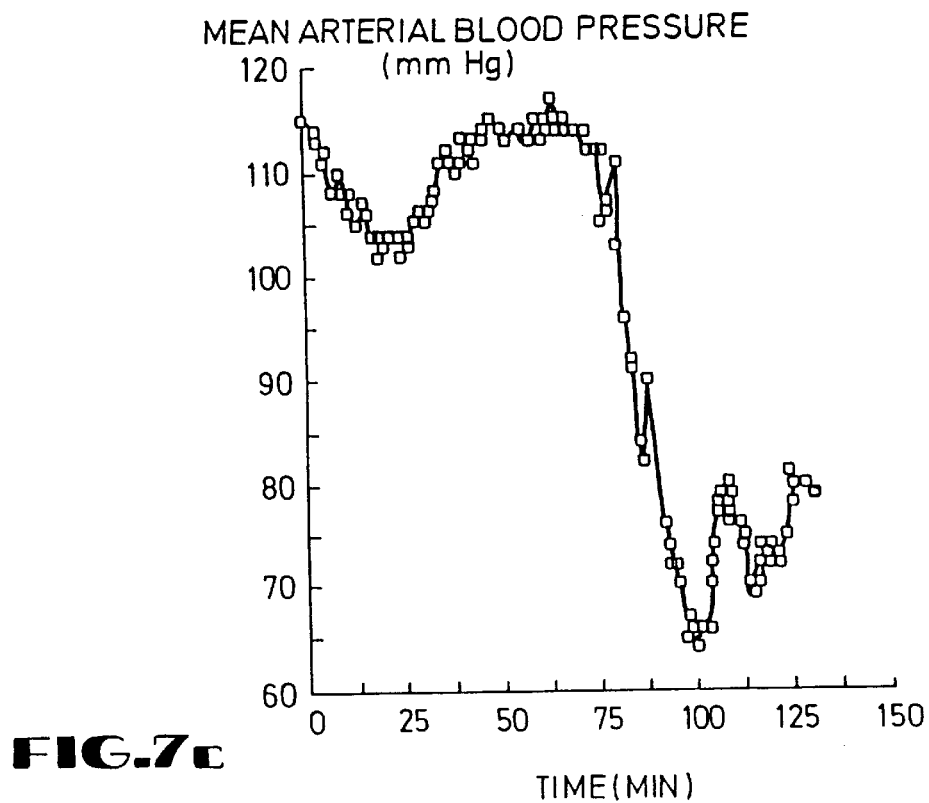
Figure 8A:
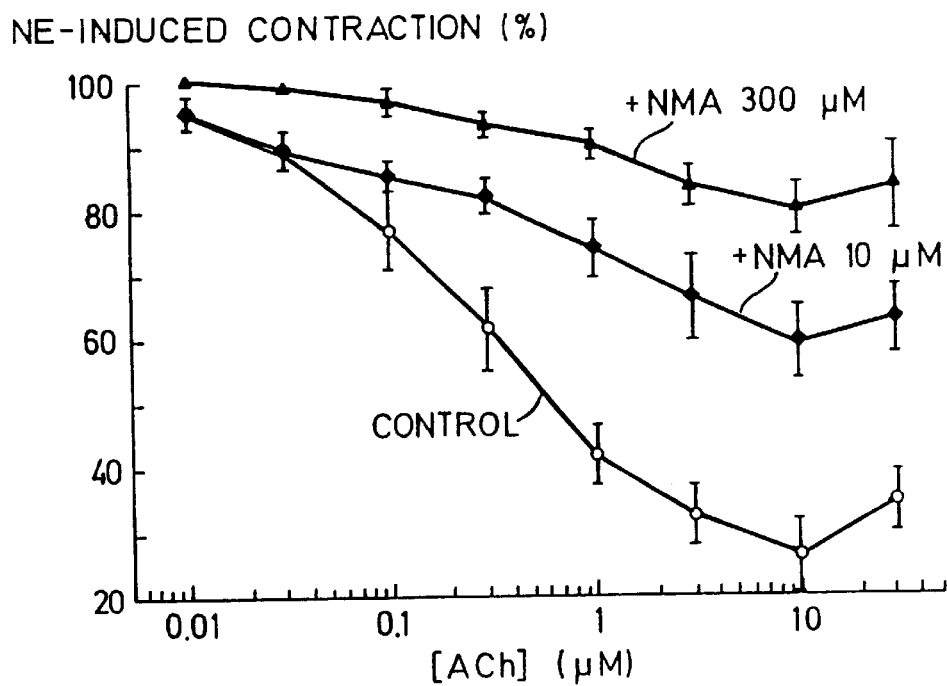
Figure 8B:
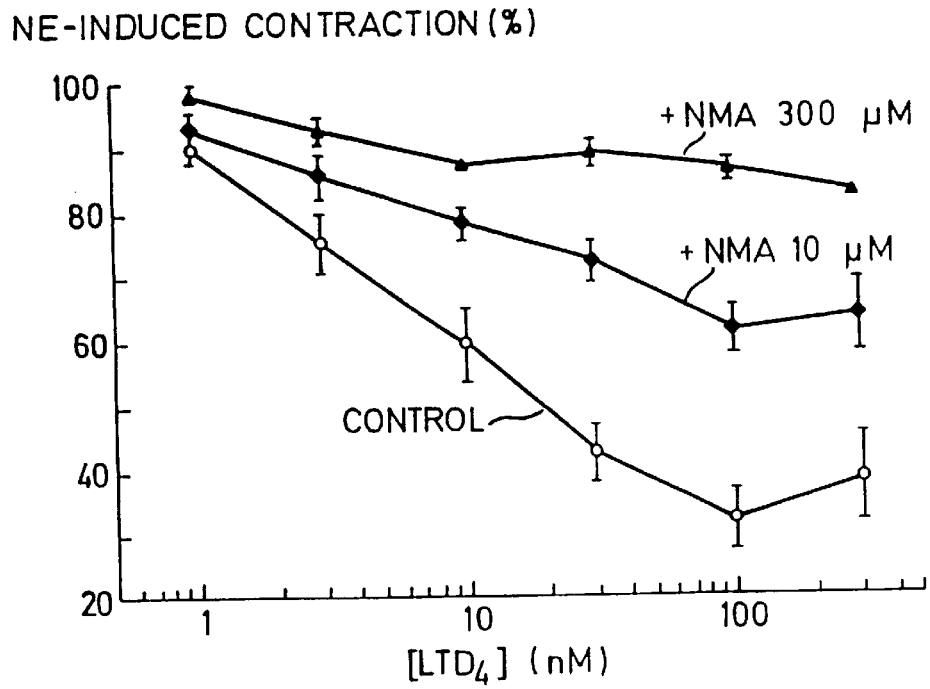
Figure 8C:
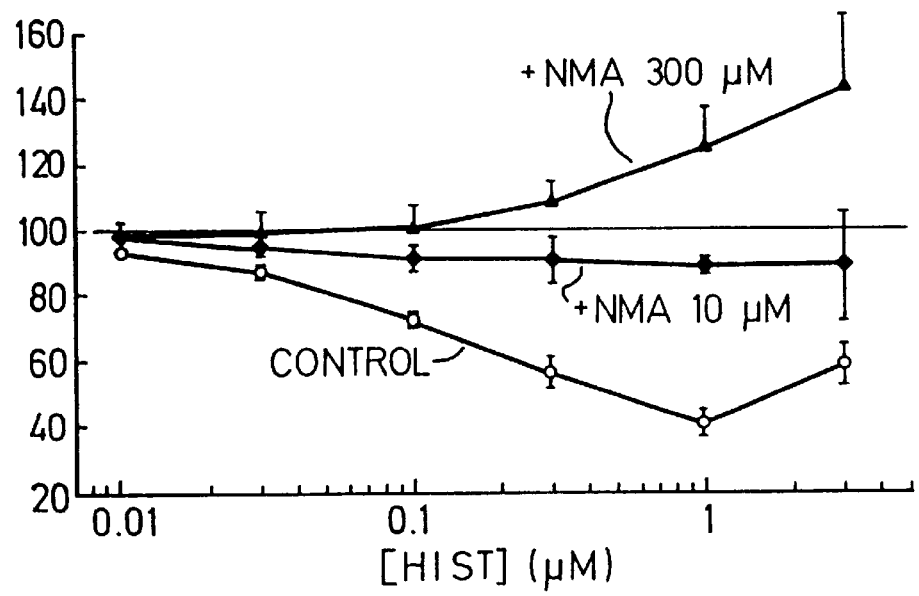
Figure 8D:
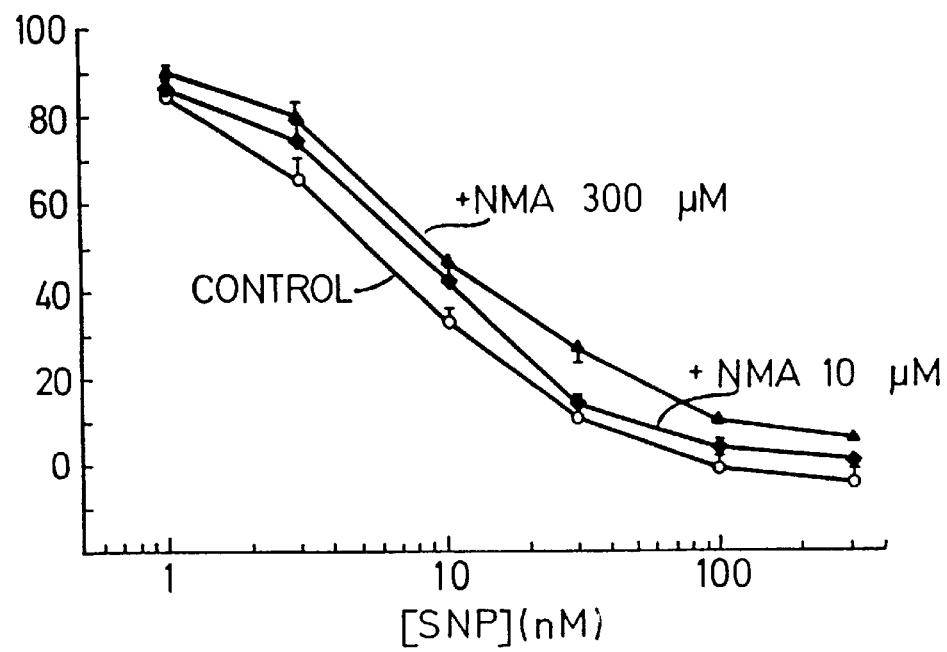

FIG. 7c illustrates the effects of NMMA on nitroglycerin-induced canine hypotension.

FIGS. 8a–d demonstrate the effect of NMMA on endothelium-dependent relaxation of guinea pig (cavian) pulmonary artery rings in response to ACh, $LTDD_4$, and HIST, and on endothelium-independent relaxation caused by SNP.

Figure 9:
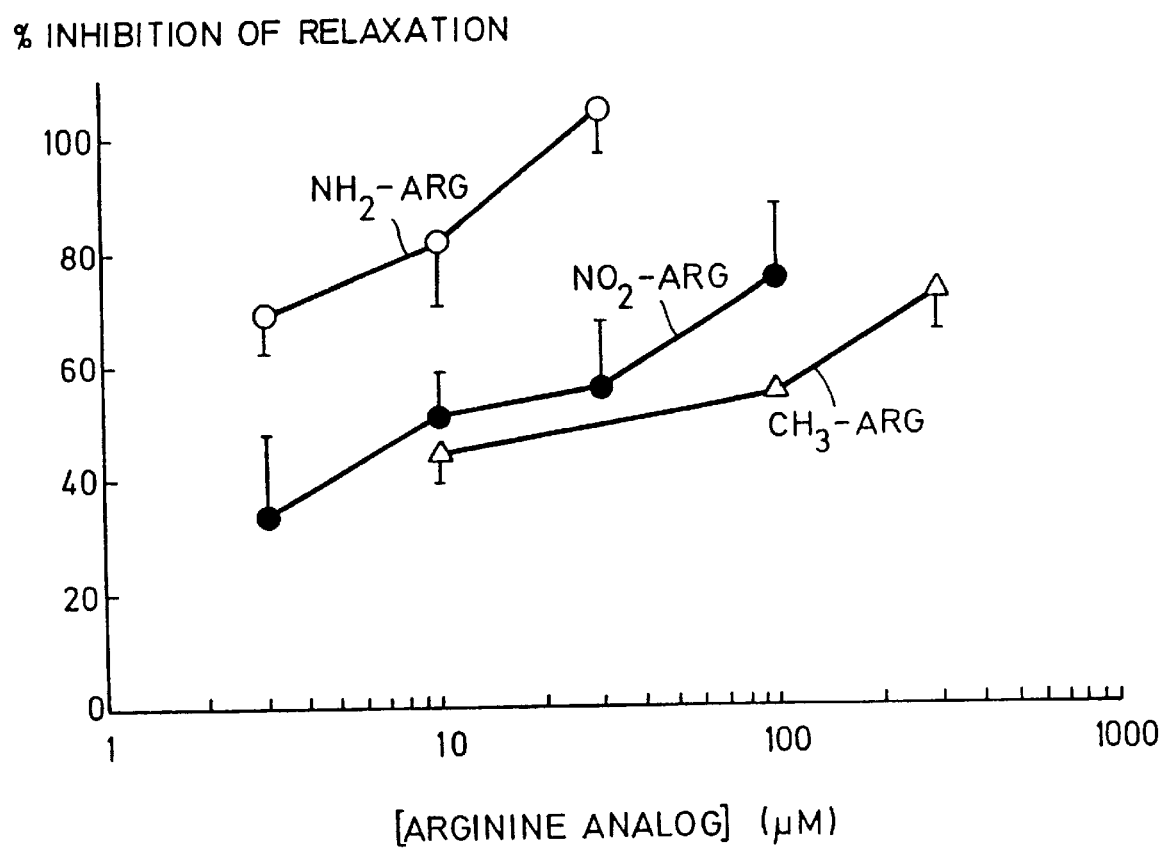

FIG. 9 shows artery ring acetylcholine-induced relaxation dose-response inhibition curves for certain $N^G$ substituted arginine derivatives.

Figure 9A:
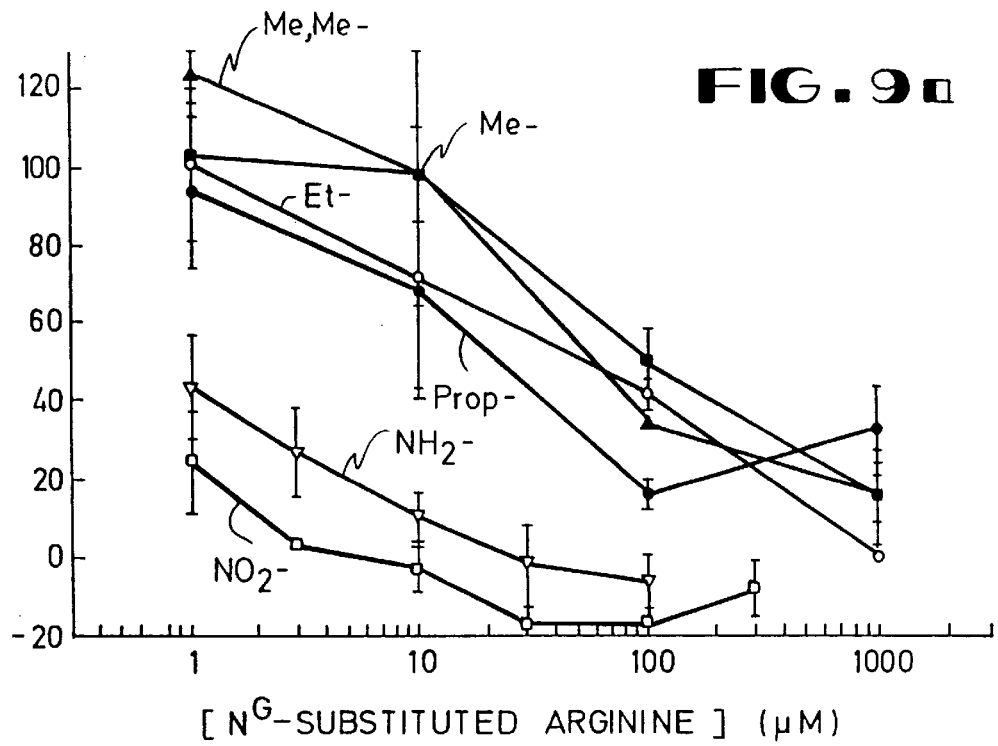

FIG. 9a shows inhibition of A23187-stimulated nitrite release in bovine aortic endothelial cells by several mono- and disubstituted arginine analogs.

Figure 9B:
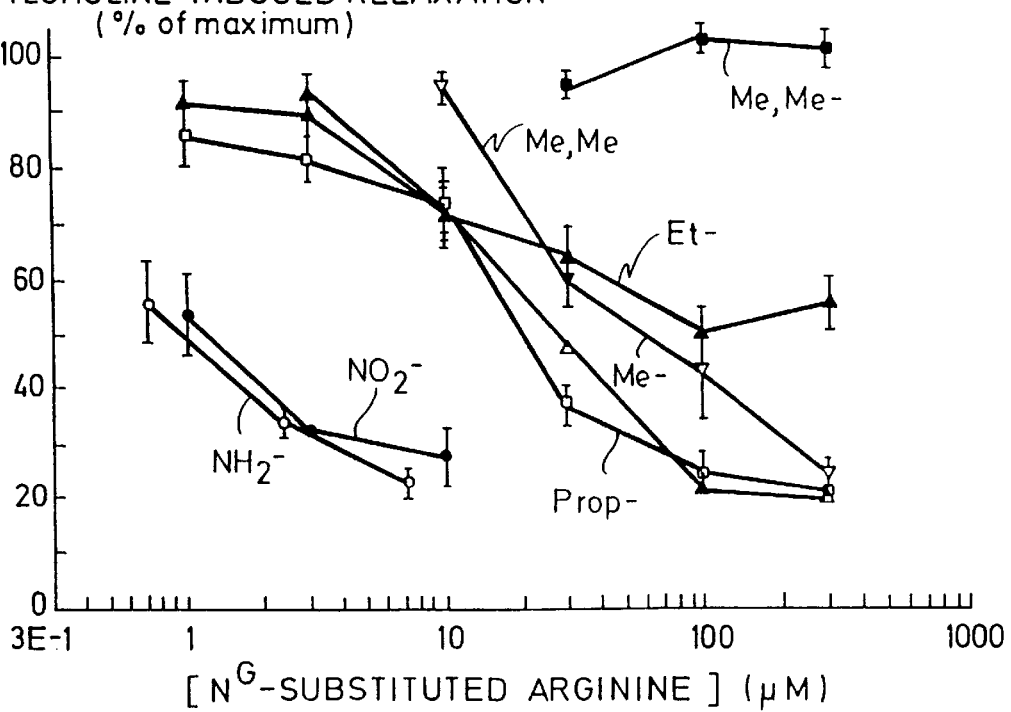
Figure 10A:
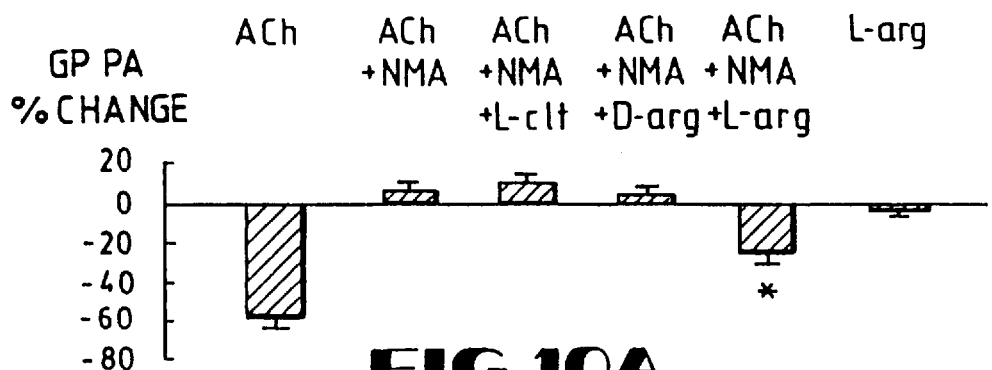
Figure 10B:
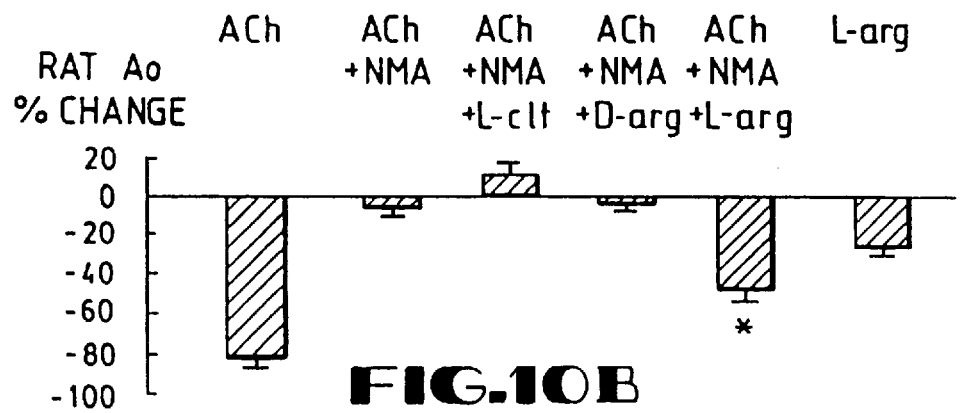
Figure 10C:
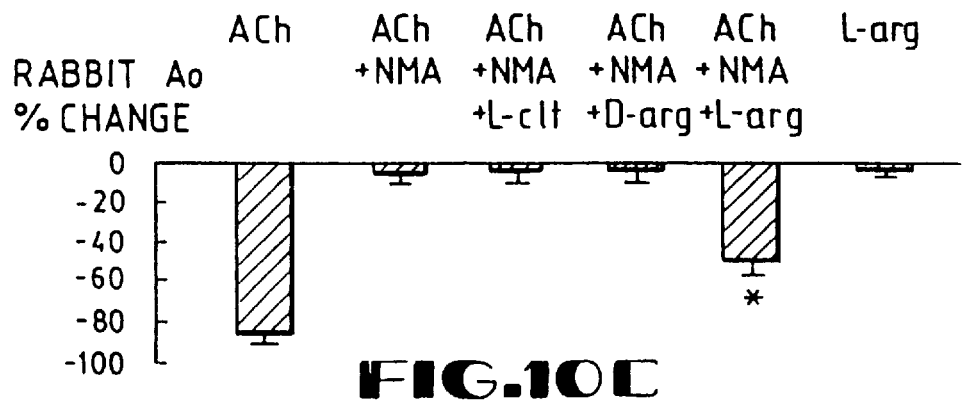
Figure 10D:
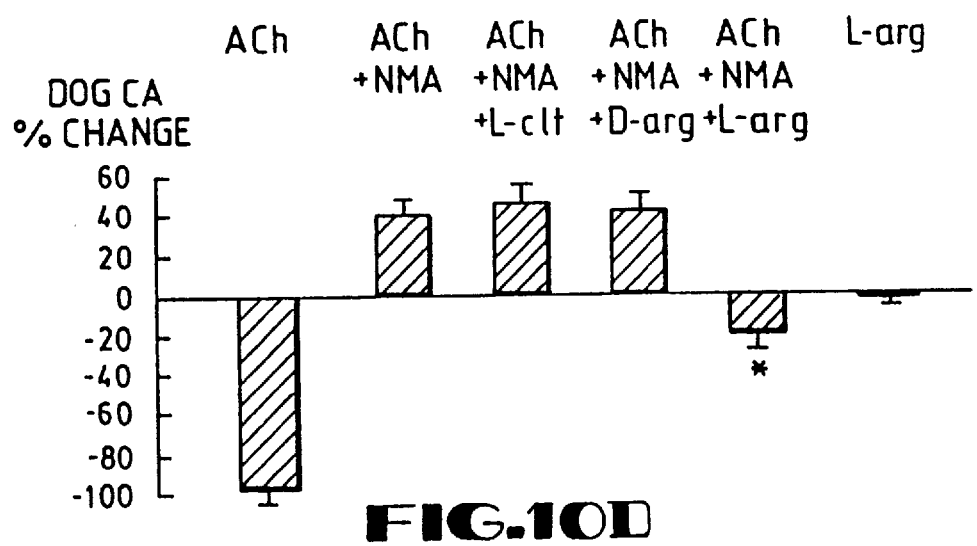
Figure 10E:
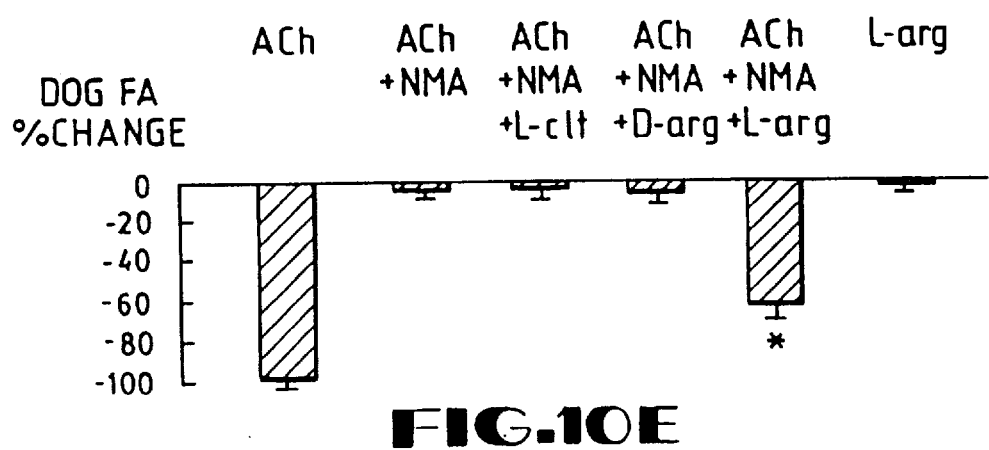

FIG. 9b shows inhibition of ACh-induced relaxation in isolated rabbit aortic rings by several mono- and disubstituted arginine analogs.

FIGS. 10a–e show the modification of ACh-induced relaxation by NMMA, L-citrulline, D-arginine and L-arginine in vascular rings from various species.

FIGS. 11a–b depict ACh-induced relaxation of NE-preconstricted rabbit aorta and human internal mammary artery as modified by L-NMA, D-arginine (D-arg), L-citrulline (L-cit) and L-arginine (L-arg).

Figure 12:
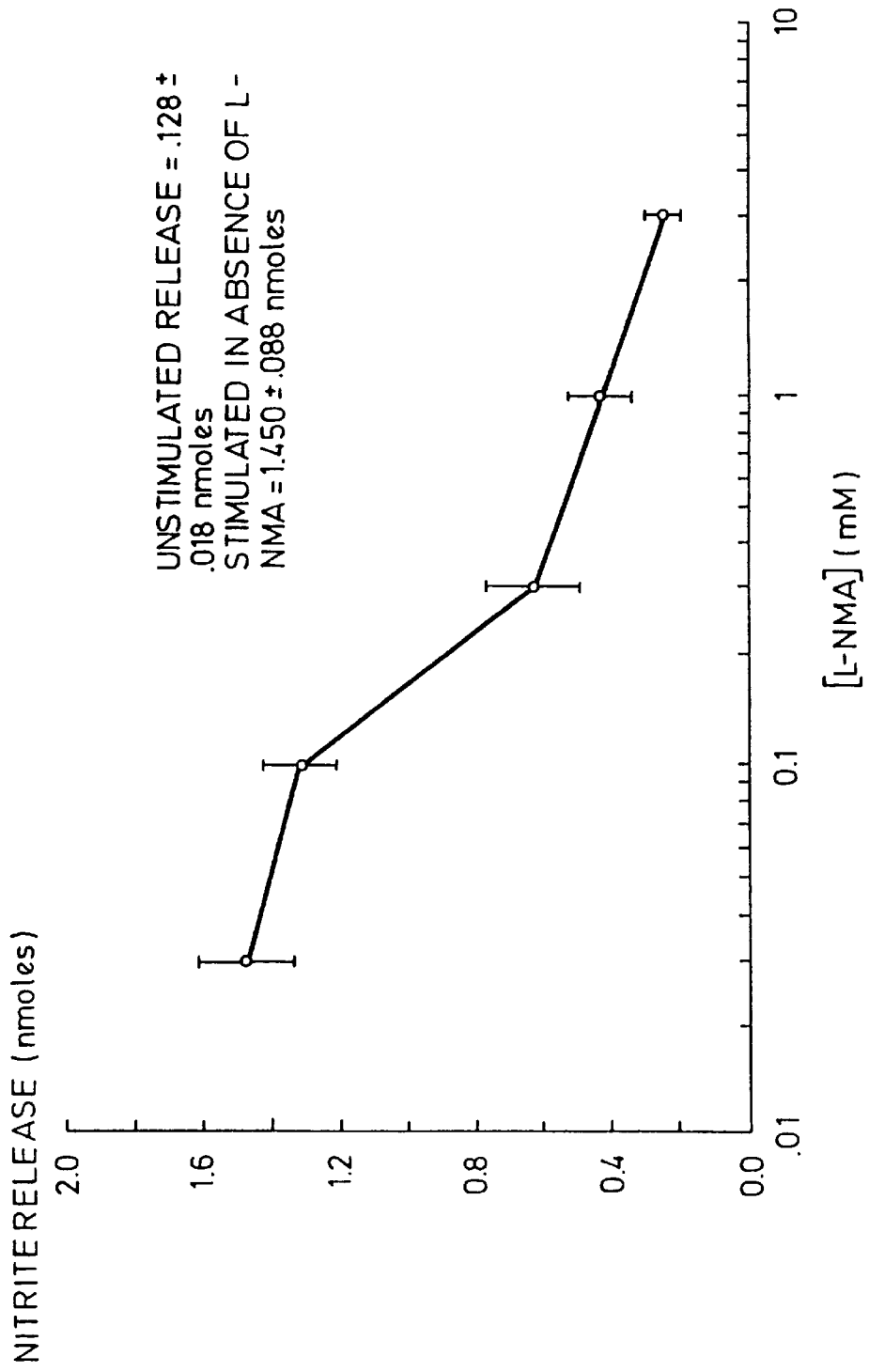

FIG. 12 shows the inhibition by NMMA of calcium ionophore induced nitrite release from bovine aortic endothelial cells (BAEC's).

Figure 13:
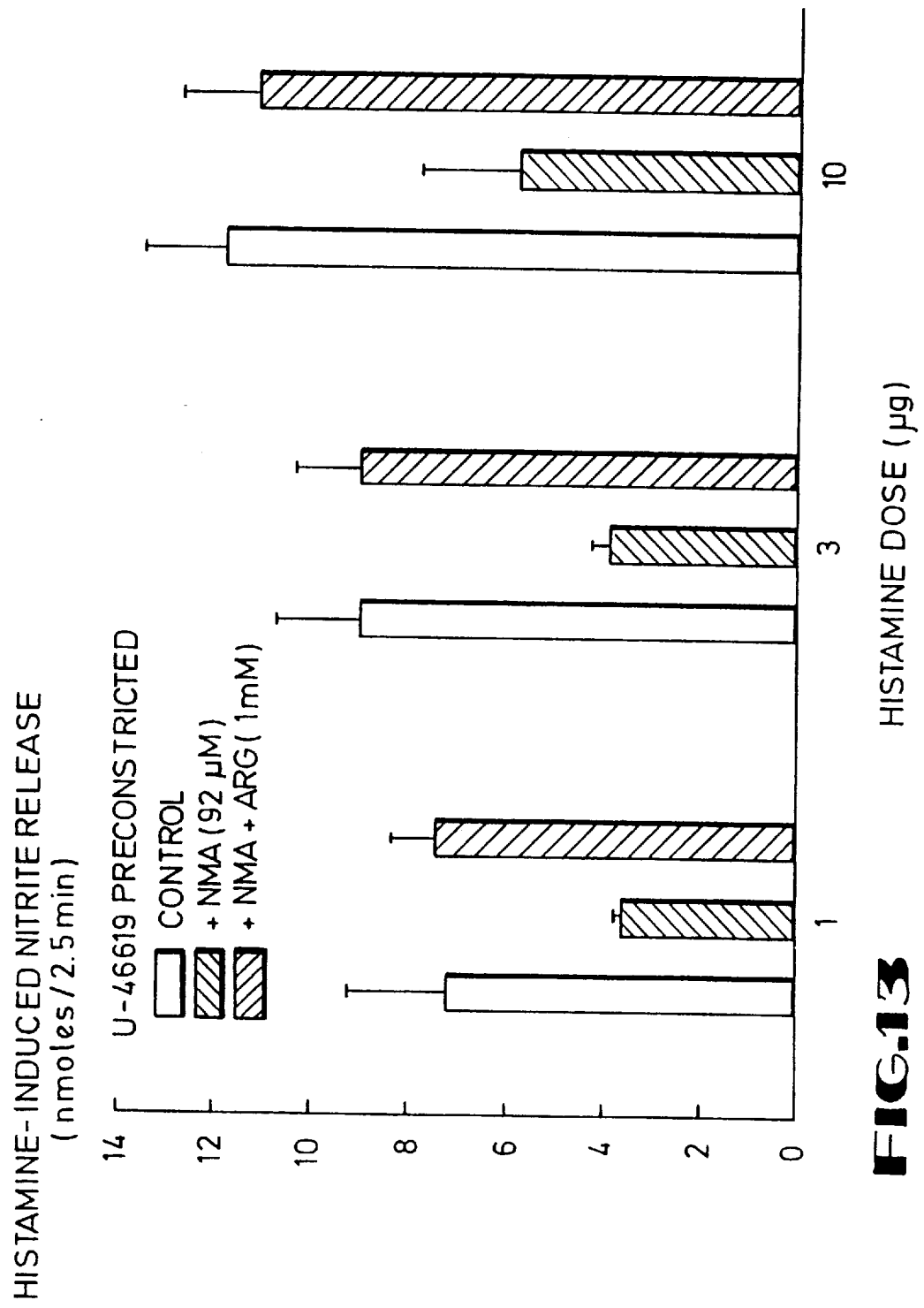

FIG. 13 shows histamine-induced nitrite release from cavian heart: blockade by NMMA and restoration by L-arginine.

Figure 14:
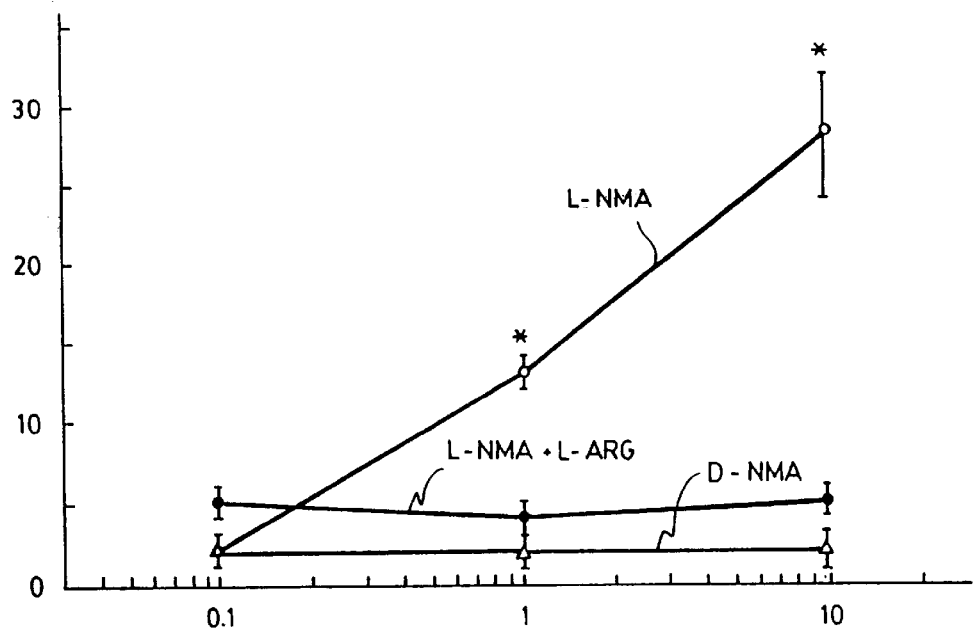

FIG. 14 shows the dose-response relationship for the pressor effect of NMMA in the anesthetized guinea pig.

Figure 15:
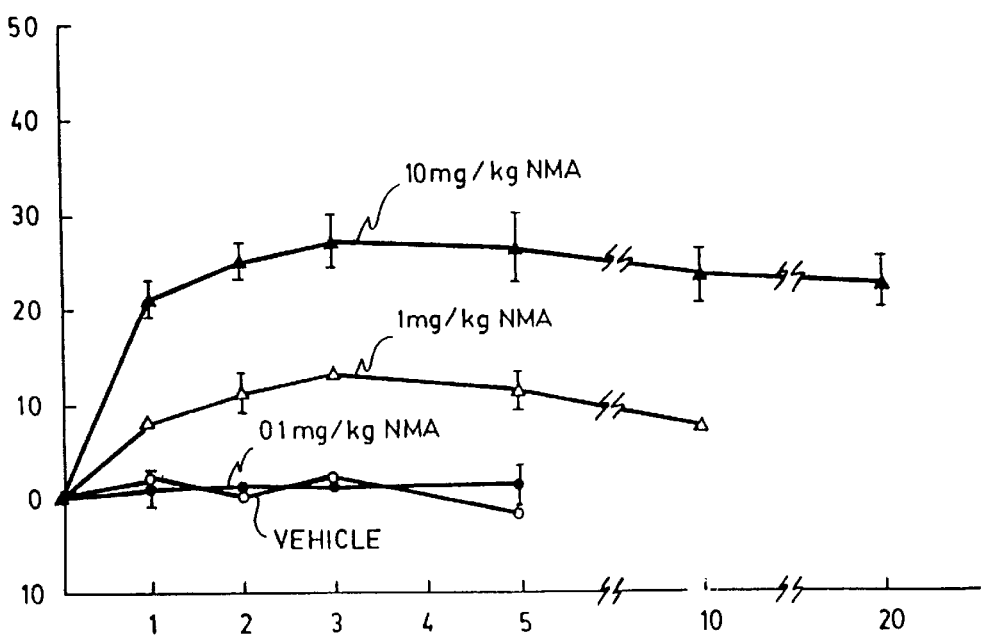

FIG. 15 shows the time course and dose-dependence of NMMA hypertension in the guinea pig.

Figure 16:
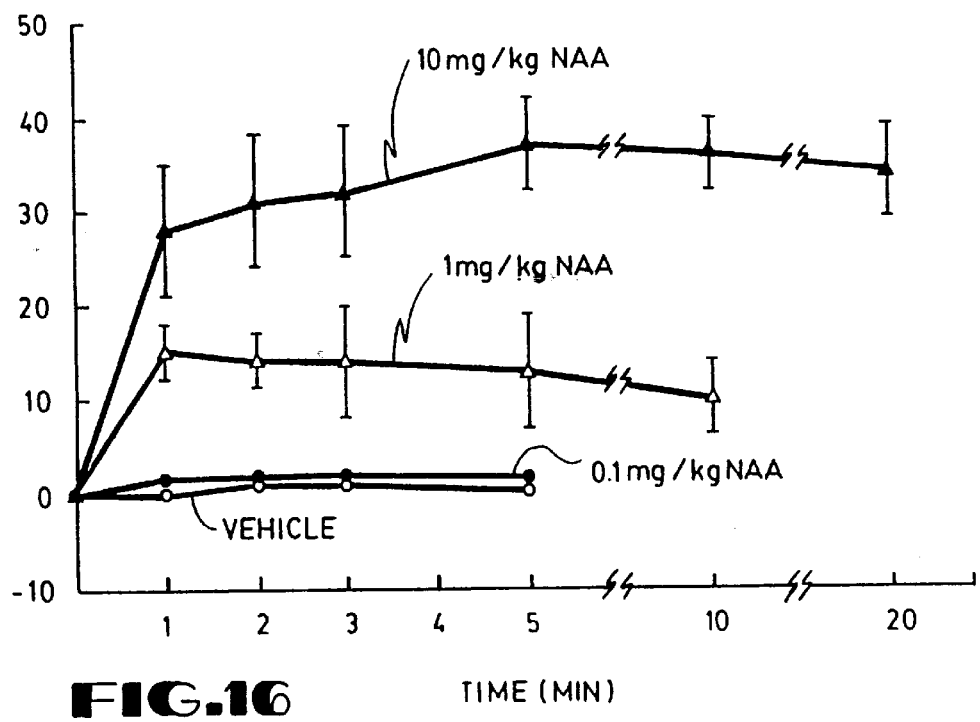

FIG. 16 shows the time course and dose-dependence of $L-N^G$-aminoarginine-induced hypertension in the guinea pig.

Figure 17:
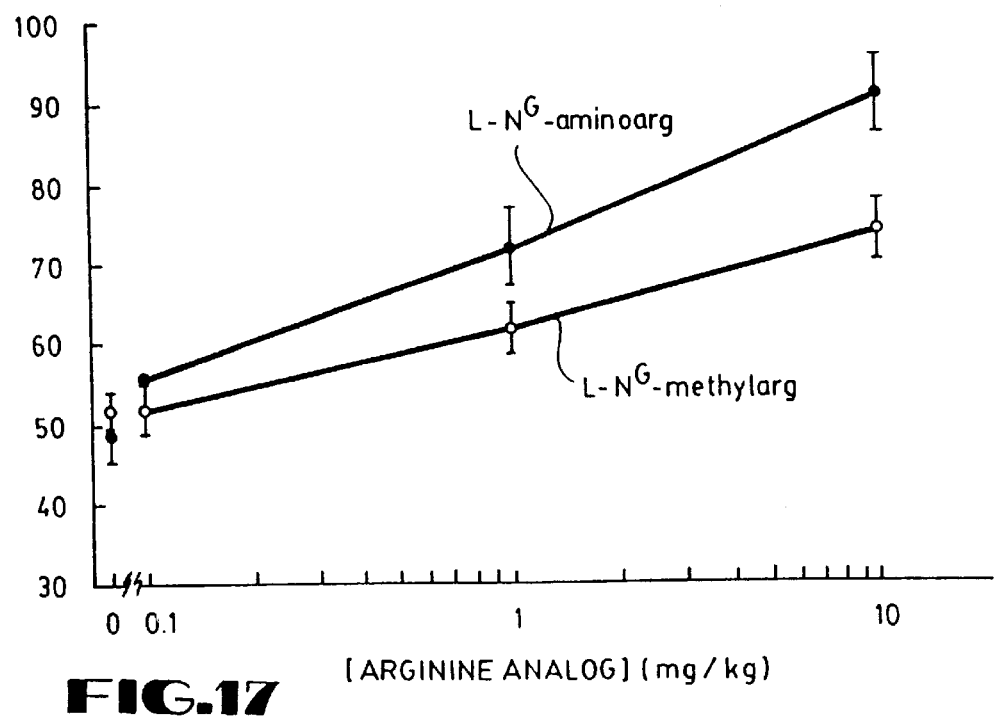

FIG. 17 shows the pressor effects of $L-N^G$-aminoarginine and NMMA as a function of concentration in the guinea pig.

FIG. 18 shows the effect of IFN and ET stimulation of EMT6 cells on cytosol nitrite concentration in these cells.

FIG. 19 shows that nitrite formation in the cytosol of EMT6 cells stimulated by IFN and ET is dependent upon arginine and NADPH.

Figure 20:
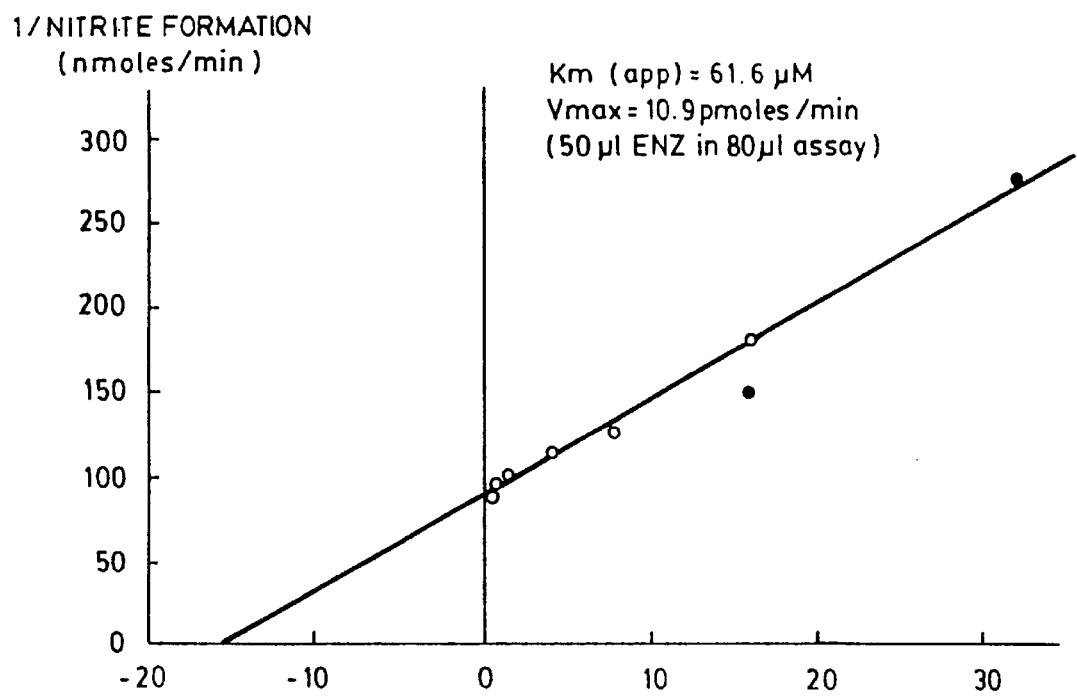

FIG. 20 is a Lineweaver-Burke plot for L-arginine-dependent nitrite synthesis by an enzyme activity present in stimulated EMT6 cytosol (stimulated with IFN and ET).

Figure 21:
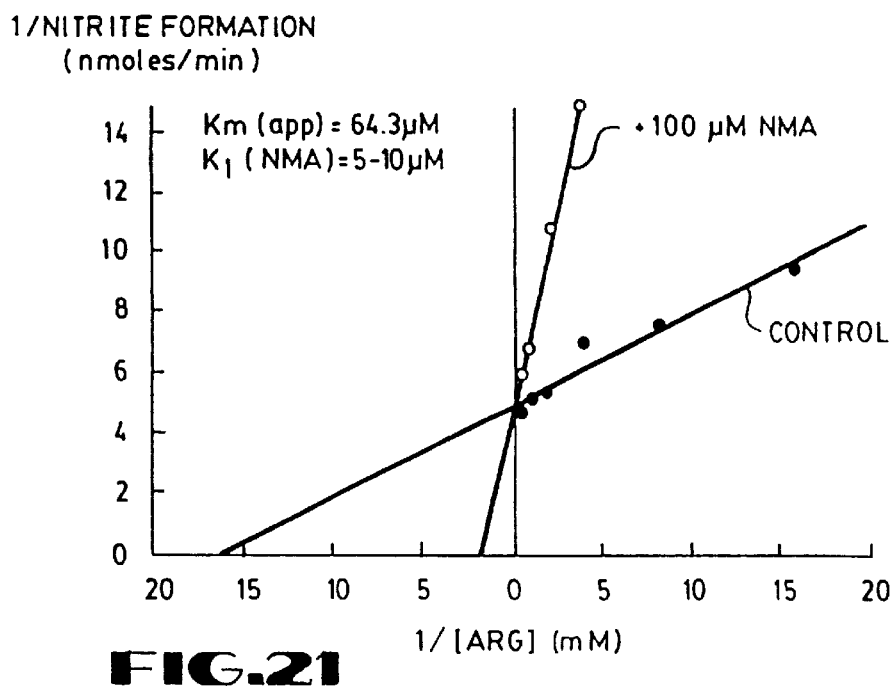

FIG. 21 shows that NMMA is a competitive inhibitor of the enzyme described in FIG. 20.

Figure 22:
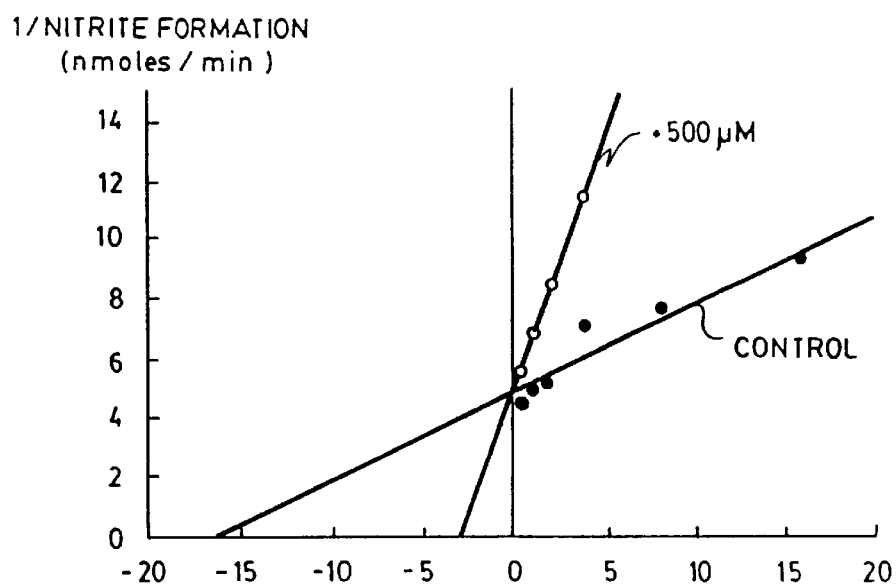

FIG. 22 shows a Lineweaver-Burke plot indicating that $N^G$-monoethylarginine (L-NEA) is a competitive inhibitor of the enzymic activity shown in FIG. 20.

Figure 23:
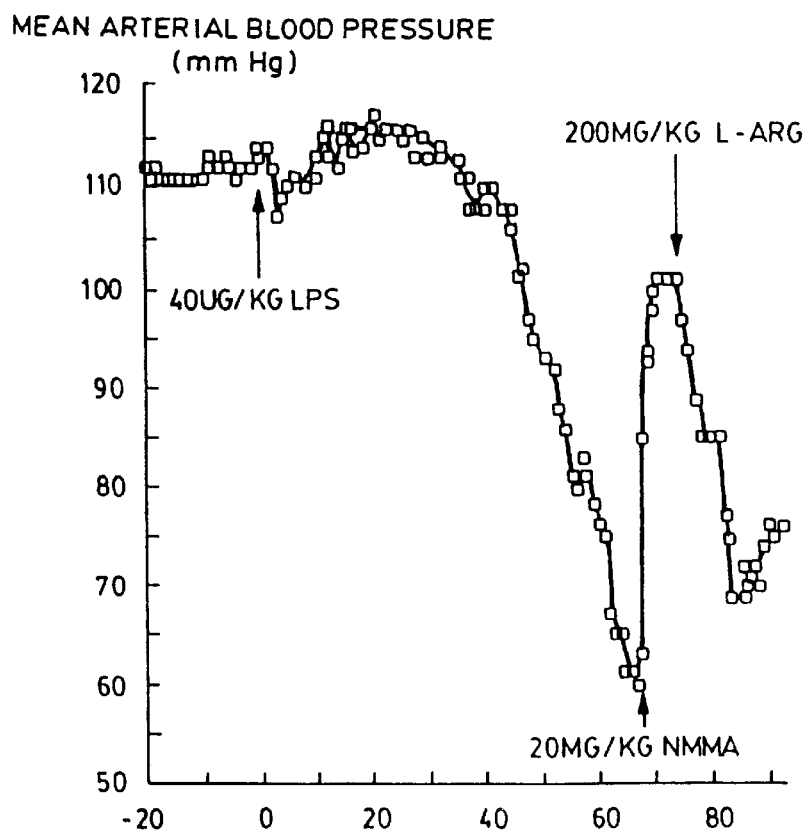

FIG. 23 shows the time course of changes in mean systemic arterial pressure (SAP) in a pentobarbital-anesthetized dog following the i.v. administration of endotoxin (ET), $N^G$-methyl-L-arginine (L-NMA), and L-arginine (L-Arg).

Figure 24:
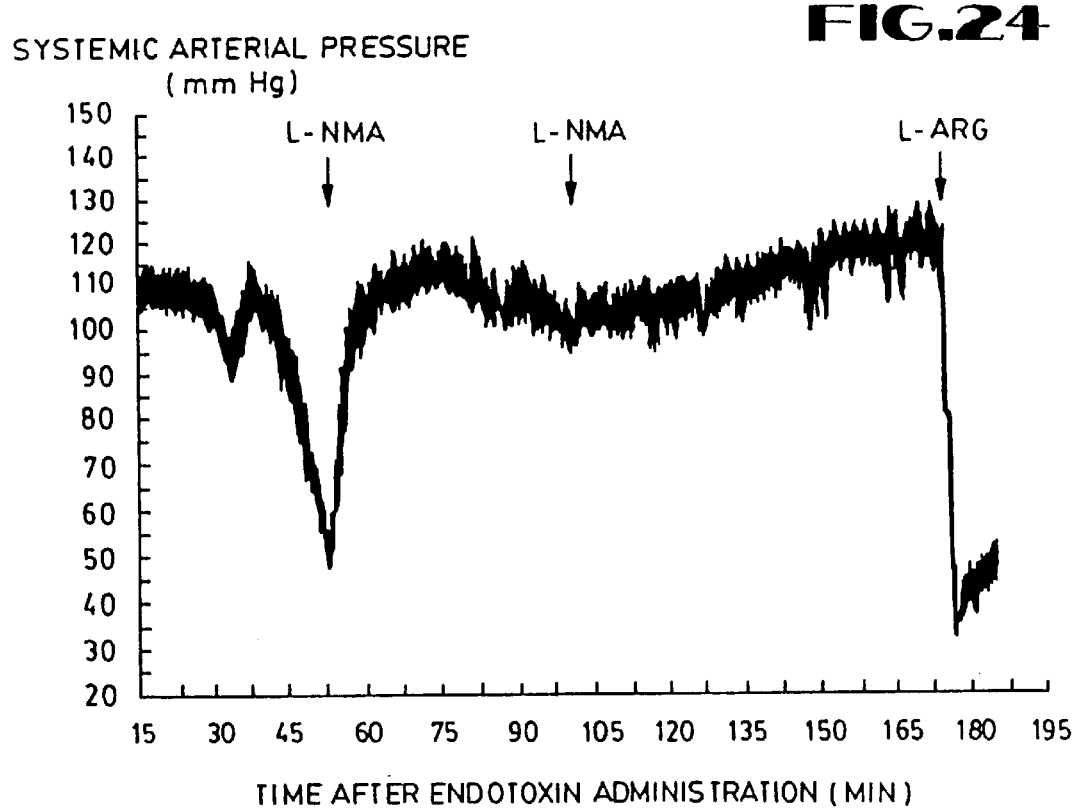

FIG. 24 shows the time course of changes in mean systemic arterial pressure (SAP) in a pentobarbital-anesthetized dog following the i.v. administration of endotoxin, L-NMA and L-ARG.

Figure 25:
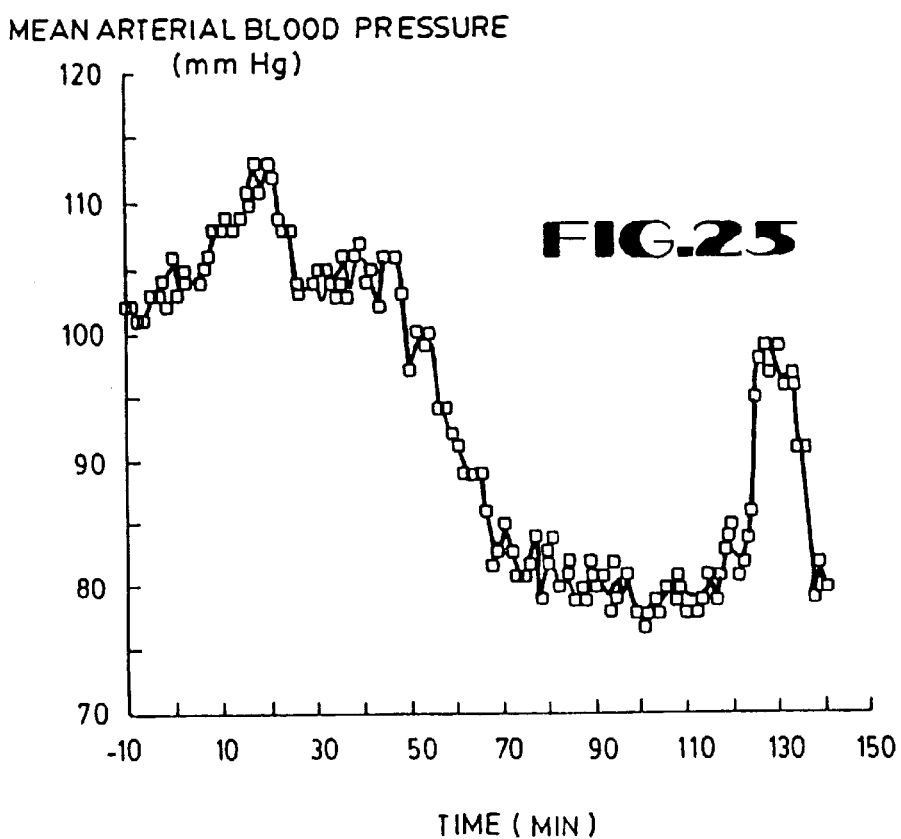

FIG. 25 shows the time course of TNF-mediated canine systemic hypotension and reversal by $N^G$-aminoarginine.

Figure 26:
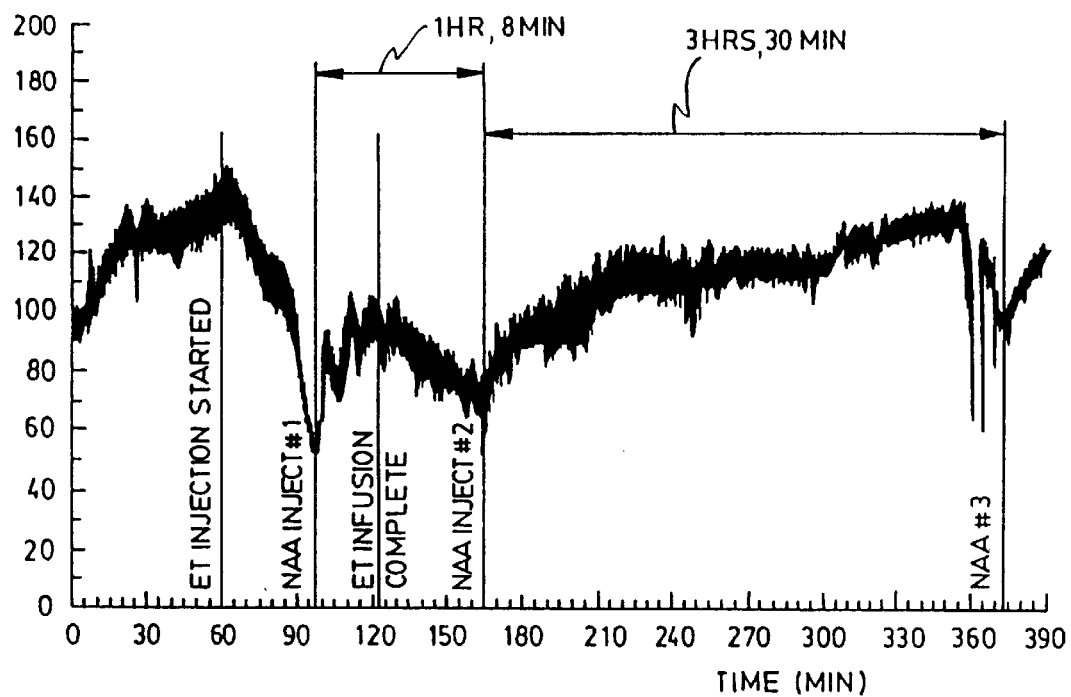

FIG. 26 shows the reversal of endotoxin-induced systemic hypotension by $N^G$-aminoarginine.

Figure 27:
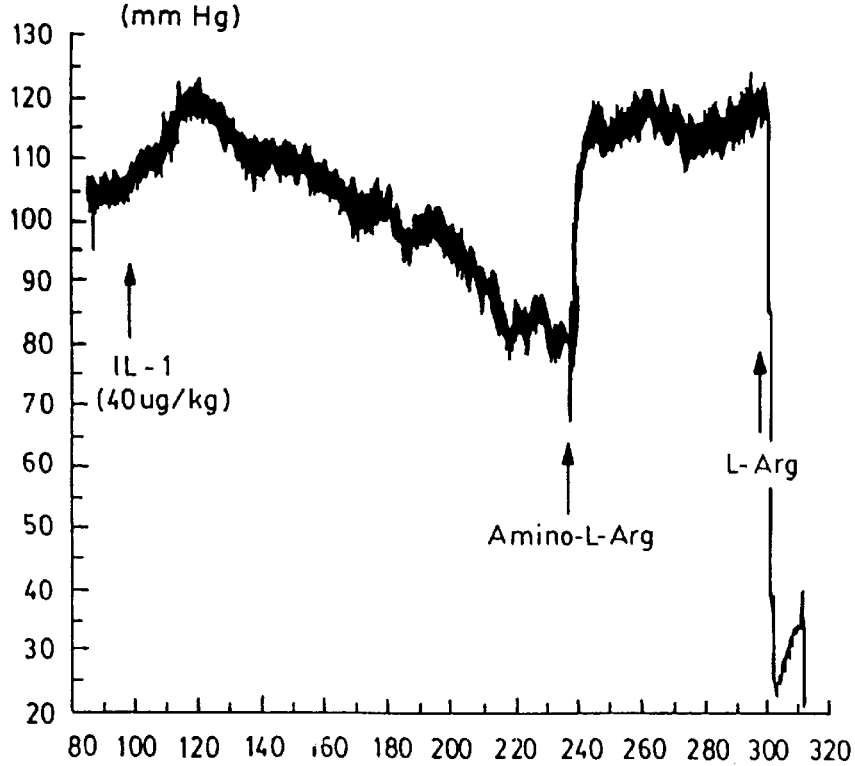

FIG. 27 shows the reversal of interleukin-1 mediated hypotension by $N^G$-aminoarginine.

Clinical studies of biologic response modifiers such as certain cytokines have shown that a major dose-limiting toxicity is hypotension. These cytokines have also been found to activate macrophages, a process that renders macrophages cytotoxic for tumor cells. Recent studies have implicated macrophage-derived nitric oxide, as the effector molecule responsible for tumor cell cytotoxicity. Nitric oxide (NO) is a highly reactive compound which spontaneously decomposes to nitrates and nitrites in the culture medium. Nitrite, a predominant spontaneous oxidation product of NO is readily assayed and used herein for assays of NO production. NO has also been demonstrated to be produced by vascular endothelial cells, previously being known as endothelial-derived relaxing factor (EDRF). EDRF has been found to cause relaxation of the smooth muscle of arteries in response to the infusion of hypotensive agents such as bradykinin or acetylcholine.

The present invention involves a finding that IFN (100 U/ml) in combination with either TNF 500 U/ml), IL-1 (10 U/ml), or endotoxin 1 $\mu$g/ml.), can induce MBEC's to accumulate nitrate in the culture medium (15 to 80 $\mu$M in 48 hours). These levels are comparable to those produced by activated macrophages. TNF, IL-1 or endotoxin alone induced the production of minimal levels of nitrites (1–3 $\mu$M).

The release of vasoactive factors such as NO by endothelial cells may play a role in the development of hypotension associated with the administration these agents in vivo. This invention relates to a demonstration that cultured MBEC's produce NO in response to various combinations of cytokines and the potential role of NO in the pathogenesis of vascular endothelial cell injury.

These examples are presented to describe the best mode, preferred embodiments and utilities of the present invention and are not meant to limit the present invention unless otherwise stated in the claims appended hereto.

EXAMPLE 1

Materials—Recombinant murine IFN, IL-1 and TNF (Genzyme). NMMA was a gift from Dr. Moncada, London, England. Endotoxin (*E. coli* B126) and all other reagents were obtained from the Sigma Chemical Co. (Sigma).

Endothelial cells—MBEC's were isolated from murine brain microvessels and cultured on gelatin-coated tissue culture dishes in DME/F12 media supplemented with 2% PPPHS, 5% FBS (Hyolone), 50 $\mu$g/ml ECGF (Biomed Tech), and 10 U/ml heparin (Sigma) as previously described (Belloni et al. 1989). The endothelial derivation of MBEC's was determined by the presence of a non-thrombogenic surface to platelets and immunofluorescent staining for Factor VIII related antigen. MBEC's were used between passage 6–9 for all experiments.

Nitrite Assay—MBE cells were cultured on gelatin-coated well plates (Corning) in 100 $\mu$l of culture medium and treated with cytokines at 3 days post-confluence. After 48 hours, nitrite production was determined by a colorimetric assay. Briefly, 50 $\mu$l of media was removed from each culture well and mixed with 50 $\mu$l of Greiss reagent (1% sulfanilamide and 0.1 % naphthyethylene diamine dihydrochloride in 2% $H_3PO_4$, incubated for 10 minutes with shaking at 25', and the absorbance (OD) was measured in a microplate reader (Molecular Devices Corp.) and concentrations determined by comparison to a standard solution of $NaNO_2$ in water. Background nitrite levels in control cultures not receiving cytokines were subtracted from the experimental values. In certain experiments NMMA was added to the growth medium at the time of cytokine addition, while in others arginine-free media was supplemented for the growth medium. All treatments were performed in triplicate and data presented as the mean value±standard deviation.

Effect of Cytokines on Nitrite Production by MBEC

Figure 1:
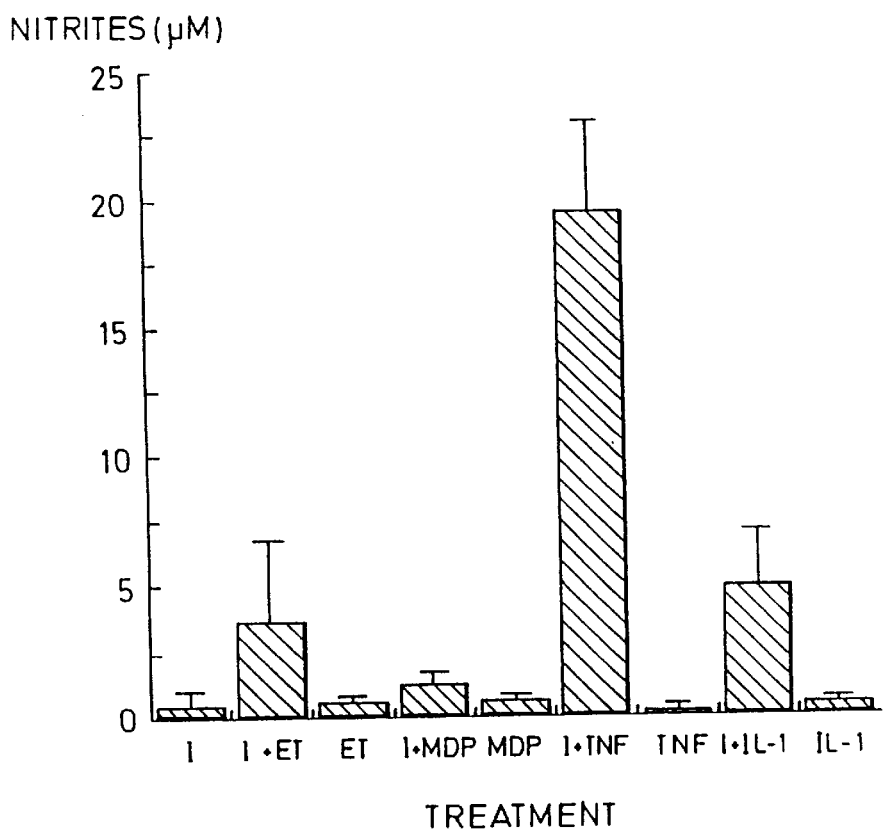
Figure 2A:
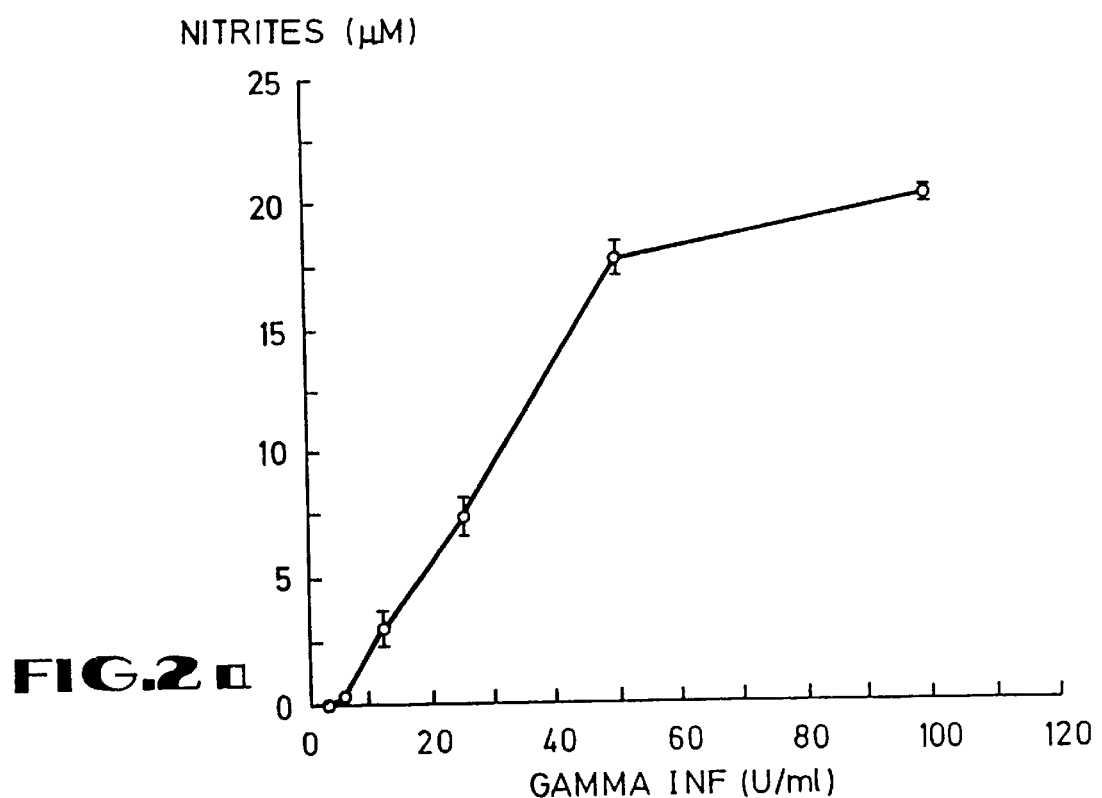
FIG. 2a shows nitrite concentration associated with MBEC at constant tumor necrosis factor (TNF) concentration and a range of IFN concentrations.
Figure 2B:
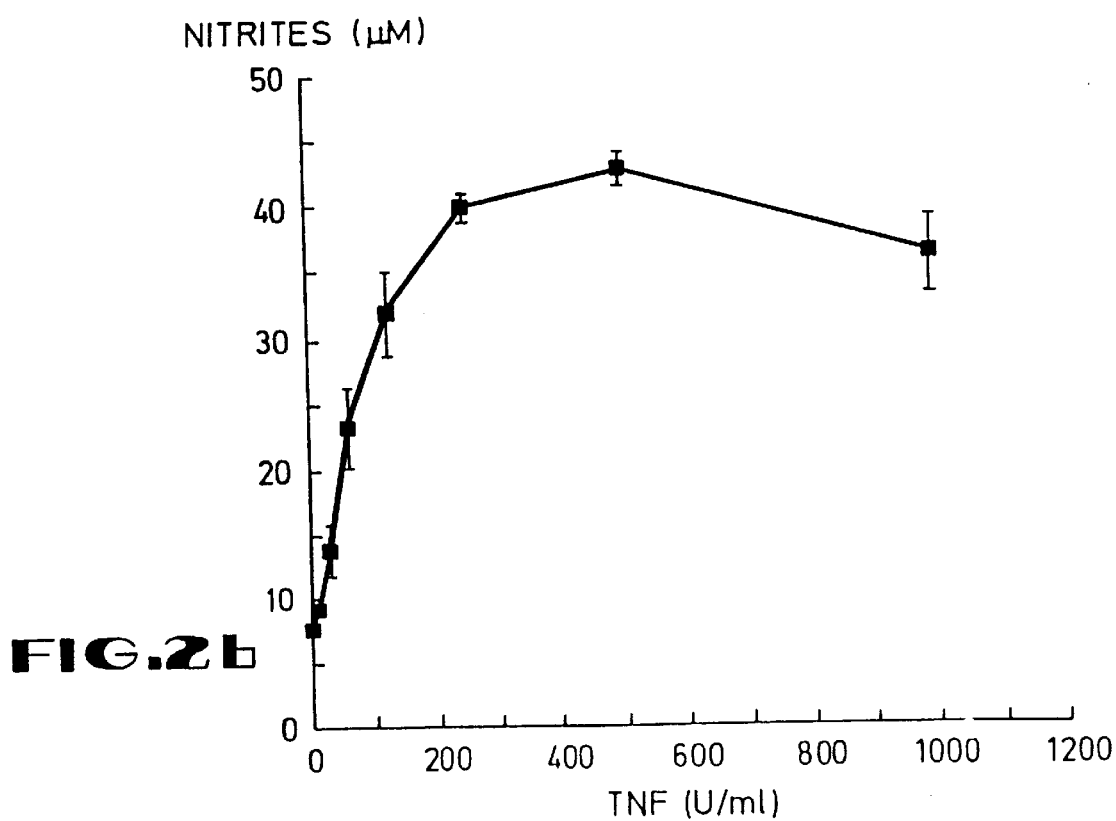
FIG. 2b shows nitrite concentration associated with MBEC at constant IFN concentration and a range of TNF concentrations.

The effects of IFN in combination with various cytokines or immunomodulators on the production of nitrite by MBEC are illustrated in FIG. 1. Exposure of endothelial cells to IFN (100 U/ml) alone had no effect on nitrite production, however combinations of interferon with TNF (500 U/ml), Il-1 (10 U/ml) or endotoxin (1 μg/ml) resulted in a synergistic effect on nitrite production compared with the effects of these agents alone. Neither muramyl dipeptide (MDP) or Il-2 alone, or in combination with IFN effected nitrite production by MBEC. This lack of response distinguishes the MBEC's from activated macrophages which produce significant amounts of nitrites after exposure to MDP and IFN (Drapier et al. 1988). IFN plus TNF was the cytokine combination found to most effectively induce nitrite production (19.5 mM±5). Dose response curves for TNF and IFN are shown in FIGS. 2a and 2b. The accumulation of nitrites was proportional to the concentration of TNF added when IFN was present at a concentration of 100 U/ml (FIG. 2b).

Figure 3:
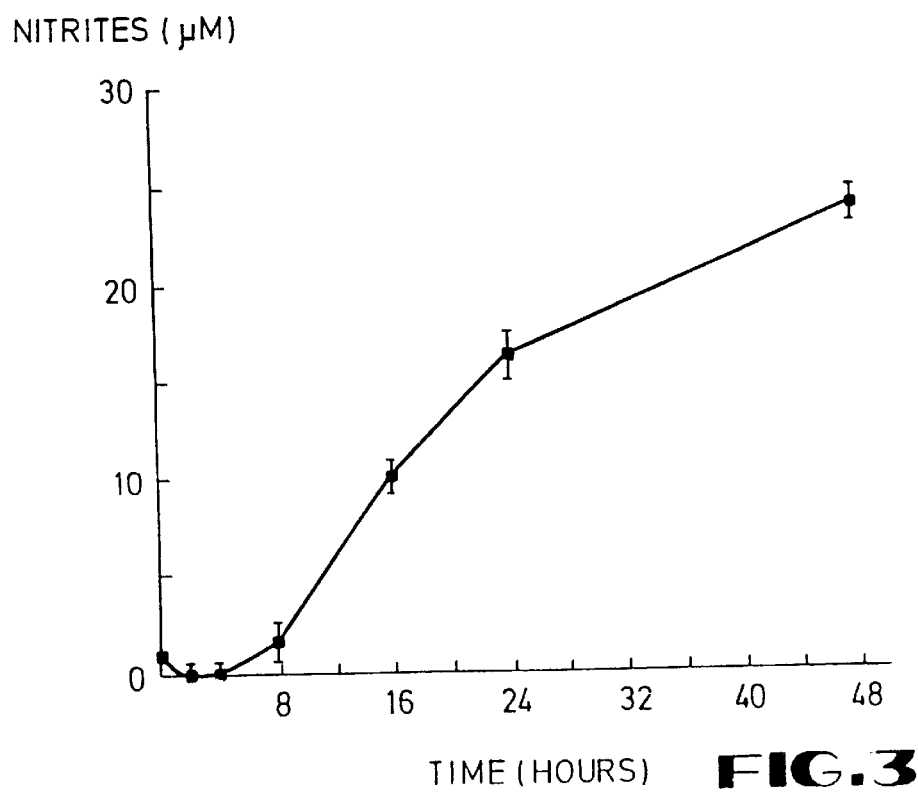
FIG. 3 shows nitrite concentration associated with MBEC induced by TNF and IFN (as a function of time).

The accumulation of nitrites in the culture medium was also found to occur in a time dependent manner with the first detectable increase at 8 hours after addition of TNF and IFN (FIG. 3). The maximum accumulation was observed at 48 hours and therefore, in all subsequent studies nitrite measurements were performed 48 hours after the addition of TNF (500 U/ml) and IFN (100 U/ml). Although both TNF and IFN have been reported to cause morphological alterations in human umbilical cord endothelial cells, no changes in the gross morphology of these murine microvascular endothelial cells was detected under these conditions.

Arginine is Required for Production of Nitrites

Figure 4:
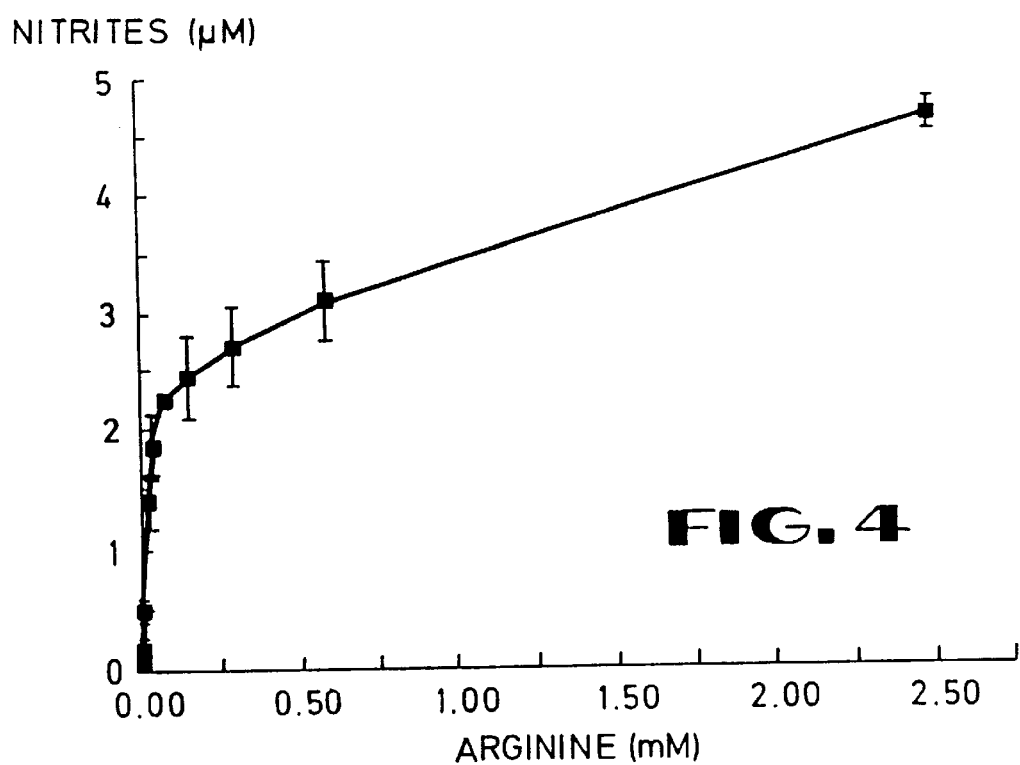
FIG. 4 shows nitrite concentration associated with MBEC exposed to TNF and IFN as a function of arginine concentration.
Figure 5:
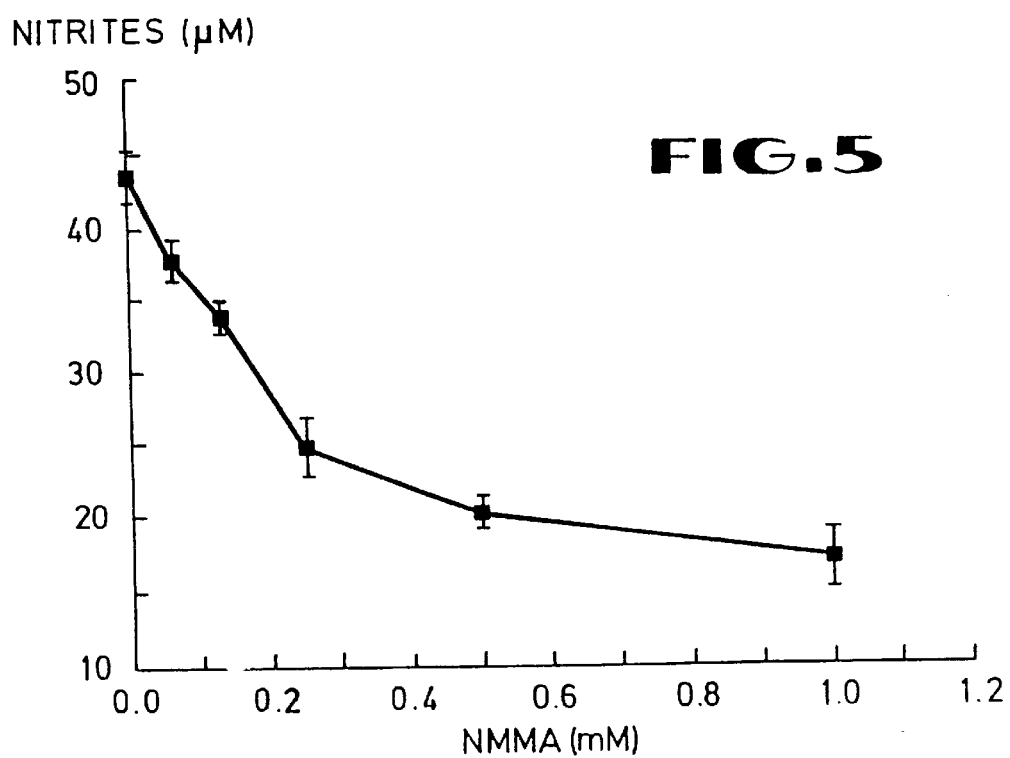
FIG. 5 shows reduction by NMMA of TNF and IFN-induced nitrite concentration associated with MBEC.
Figure 5A:
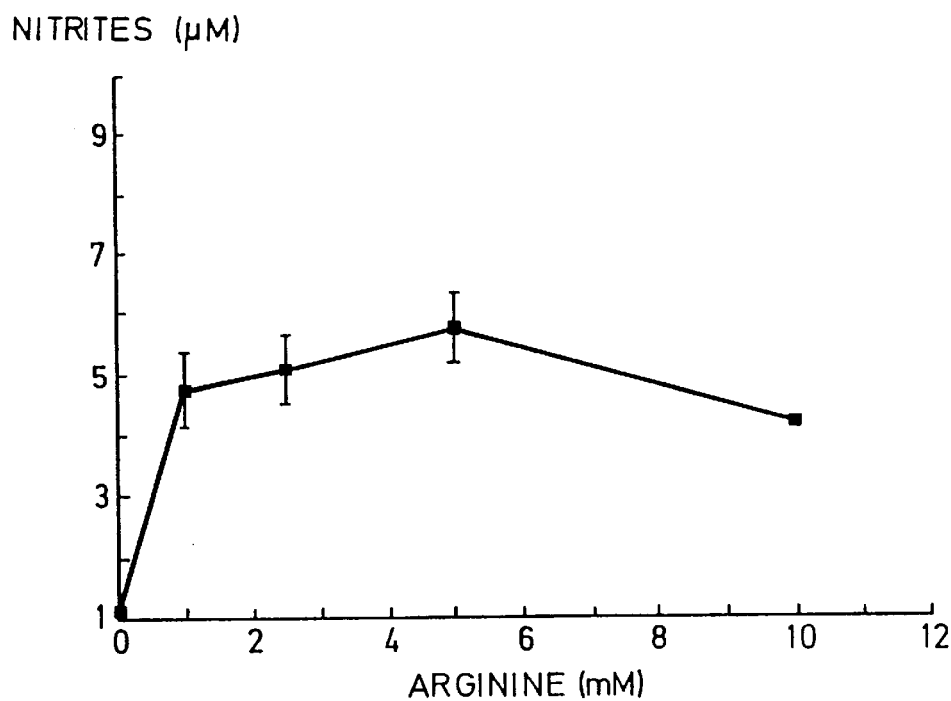
FIG. 5a shows arginine reversal of NMMA inhibition of nitrite concentration.

Increased concentrations of nitrites were not associated with MBEC exposed to TNF and IFN in arginine-free culture medium; the nitrite concentration increased in a dose dependent manner upon addition of L-arginine back to the medium (FIG. 4). Nitrite production was also inhibited by addition of the arginine derivative NMMA (FIG. 5). This inhibition was proportional to the concentration of NMMA and was maximal in the presence of 1 mM NMMA (E.D. 50%=0.33 mm). In addition, the inhibitory effect of NMMA could be reversed by the addition of excess L-arginine, with 8 mM L-arginine completely reversing the effects of 1 mM NMMA (FIG. 5a). These results suggest that microvascular endothelial cells produce NO in response to specific cytokines by de novo synthesis utilizing L-arginine as the physiological precursor. A similar metabolic pathway has been identified for the production of NO by large vessel endothelial cells in response to hypotensive agents such as bradykinin and acetylcholine (Palmer et al. 1988 BBRC 153:1251–1256; Kelm et Al. 1988).

Figure 6:
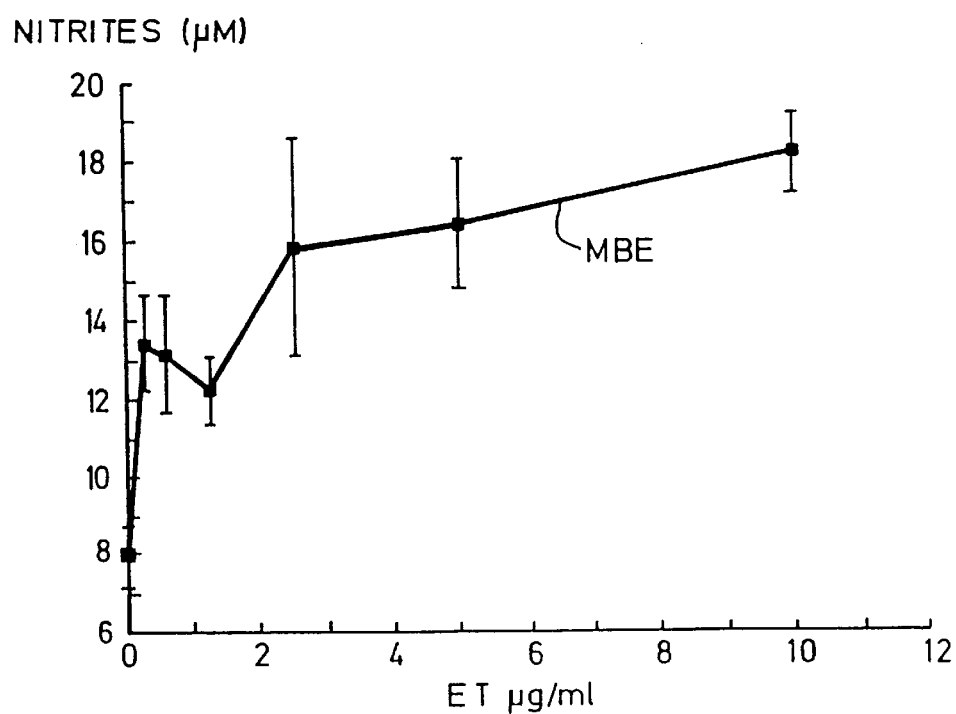
FIG. 6 shows nitrite concentrations associated with MBEC with 100 U IFN/ml as a function of endotoxin concentration.

As shown in FIG. 6, endotoxin caused a dose-dependent stimulation of nitrite production with MBEC in the presence of 100 units IFN/ml.

EXAMPLE 2

Hypotension associated with the administration of TNF in the dog can be blocked by subsequent administration of NMMA which in its free base form has the structural formula:

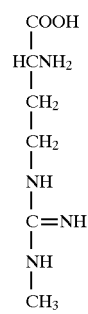

Furthermore, this inhibition of hypotension can be reversed by administration of an excess of arginine. These results show that NO is the mediator of hypotension induced by TNF. Furthermore, activation of NO synthesis may be involved in the pathogenesis of septic shock.

Reagents

Recombinant human TNF specific activity $2 \times 10^7$ units/mg, was from the Niposn Chemical Corporation, Tokyo, Japan. TNF was administered at a dose of 10 mcg/kg in a volume of 10 ml of phosphate buffered saline containing 2 mgs/ml of dog albumin. NMMA was synthesized by adaptation of the method of Corbin and Reporter (Anal. Biochem. 57: 310–312, 1974) and was dissolved in 5 ml of phosphate-buffered saline for administration at a dose of 15 mgs/kg. Arginine was obtained from Sigma Chemical Company, St. Louis, Mo.

Animals

Four conditioned mongrel dogs, 2 males and 2 females, weighing 28 to 30 kgs, were studied. Care of the animals were in accordance with the recommendation of the American Association for Accreditation of Laboratory Animals [DHEW(DHHS) publication no. (NIH) 78–23, revised, 1978]. On the day of the experiment, the dogs were fasted overnight. They were anesthetized with phenobarbital (10 mg/kg). They were then intubated orally with a #10 fr. endotracheal tube and ventilated with a Harvard pump ventilator at a rate of 12 breaths per minute and a tidal volume of 15 ml/kg. An arterial line was percutaneously placed in the femoral artery on the day of the experiment.

Physiological Measurements

Mean (electronic) and phasic systemic arterial pressures (SAP) were continuously recorded on a Hewlett-Packard recording system (model 7758B) using strain gauge manometers (Hewlett-Packard model 1290A) which were connected to the arterial line. Heart rate (HR) was determined from an EKG tracing and continuously recorded on the Hewlett-Packard recording system. Oxyhemoglobin saturation ($SaO_2$) was obtained using a pulse oximeter (BIOX 111, Boulder, Colo.). continuous time-series records of SAP, HR, and $SaO_2$ were obtained using a Lab Master analog-to-digital convertor (16 channel, 12 bit, 30 kHz; Scientific Solutions, Inc.) sampling at 55 Hz and storing the 6 sec averages on a magnetic disk.

NMMA was found to reverse the hypotension associated with the administration of TNF. The pressor effect of NMMA occurred rapidly (within 2 minutes) and could be antagonized by administration of an excess of L-arginine. The antagonism of the NMMA pressor effect was stereospecific for the L-form of arginine.

The data shown in FIG. 7 is representative of several animal experiments. There were some variations noted in the degree of hypotension as well as the time of onset of hypotension after TNF administration. Ten µg TNF/kg body weight was intravenously administered at the ten minute timepoint; 4.4 mg NMMA/kg at about 52 minutes; and 3 g L-arginine at about 63 minutes. The onset of hypotension was found to occur between 30 to 60 minutes after TNF. In dog number 3, the SAP dropped rapidly from 106 to 36. The administration of NMMA resulted in the rapid increase in blood pressure to an SAP of 116. The response of the remaining two dogs to TNF was similar to that described in FIG. 7.

The administration of NMMA alone to untreated dogs (n=3) was also tested. Within 1.7 minutes after NMMA infusion, the blood pressure initially increased. This was followed by a compensatory decrease in the HR with a return of the BP to baseline. The NMMA-induced bradycardia lasted 31 minutes. This response was not observed in animals which had been previously treated with TNF. In a subsequent experiment (FIG. 7a) the hypotensive response to TNF was especially severe, with a decrease in BP from 125 mm to 36 mmHg. Administration of NMMA resulted in an increase in the blood pressure to 115 mm, a 79 mm increase. This increase in blood pressure was completely reversed by administration of L-arginine causing the blood pressure to fall again to 37 mmHg. Control experiments in which NMMA was administered to untreated dogs are shown in FIG. 7b. Within 2 minutes the blood pressure was observed to increase by 12 mmHg. This was associated with a decrease in the HR from 101 to 92 beats/minute. Subsequent administration of L-arginine reversed these small changes observed in systemic arterial pressure. In a second control study nitroglycerin was infused at a rate of 28 µg/kg/minute, IV, to lower the blood pressure to the same level as that observed with tumor necrosis factor (FIG. 7c). After administration of NMMA in nitroglycerin infused dogs, the blood pressure increased only 14 mm. Subsequent administration of L-arginine reversed this modest effect.

The administration of L-arginine to NMMA-treated dogs resulted in the rapid decrease of blood pressure. Blood pressure was not affected by the administration of L-arginine to previously untreated dogs.

The dose-limiting toxicity of TNF administered to patients is hypotension. These experiments imply that NO, also known as EDRF, is the mediator of the hypotension. Furthermore, these hemodynamic changes can be antagonized by an $N^G$-substituted arginine derivative and subsequently restored by the addition of excess arginine, supporting a role for arginine as the substrate for NO synthesis. The present inventors have shown that NMMA can increase the resting blood pressure in the guinea pig. Therefore, NO may play a role in normal arterial pressure homeostasis. This also appears to be true in the dog.

The pressor response to NMMA is much more dramatic in dogs with TNF-induced hypotension than in normotensive dogs. This suggests that TNF induced hypotension is due to an excess production of a vasoactive factor (i.e., NO) which acts to regulate normal resting blood pressure.

TNF is also involved in the development of the toxicity observed in septic shock. Septic shock is caused by endotoxin, a component of the cell wall of gram negative organisms. The administration of anti-TNF antibodies after TNF exposure does not protect against hypotension. This implies that TNF may induce another mediator of hypotension. The results presented herein indicate that NO is the true mediator of that response.

EXAMPLE 3

L-$N^G$-substituted arginine analogs block NO synthesis from arginine. NMMA blocks endothelium-dependent relaxation in response to various dilators which act via EDRF/NO release. FIG. 8 shows concentration-response curves for relaxation of guinea pig pulmonary artery rings by endothelium-dependent and endothelium-independent vasodilators and the effect of NMMA. Vascular rings were preconstricted with 1 µM norepinephrine and relaxation was elicited by cumulative addition of acetylcholine (ACh, panel A), leukotriene D4 (LTD4, panel B), histamine (HIST, panel C) or sodium nitroprusside (SNP, panel D), alone (control), and in the presence of NMA. Points are mean values±SEM (n=4–8).

NMMA blocks the action of ACh, LTD4 and HIST, agents which vasodilate by eliciting release of EDRF, whereas NMMA does not inhibit vasodilatation by SNP (which acts directly on vascular smooth muscle). Thus, NMMA has a specific action on EDRF-mediated vasodilatation. It is noteworthy that L-arginine restored relaxation in the presence of NMMA and that the D-stereoisomer was not an inhibitor of EDRF/NO synthesis.

In this preparation of guinea pig pulmonary artery, arginine analogs with $N^G$ substitutions other than methyl also served as inhibitors of EDRF/NO synthesis. Those tested include: $NO_2$—, $NH_2$—, $CH_3$, and dimethyl- (dose-response curves for some of these are shown in FIG. 9). FIG. 9 shows concentration-response curves for inhibition of ACh-induced relaxation of guinea pig pulmonary artery rings by L-$N^G$-substituted arginine analogs. Rings were precontracted with 1 µM NE, then relaxed by cumulative addition of ACh, alone (control), and then in the presence of various concentrations of the arginine analogs N-aminoarginine, $N^G$-nitroarginine and NMMA. The % inhibition of relaxation is calculated from the maximum ACh-induced relaxation observed in the presence of the arginine analog relative to that in its absence. Points represent mean values±SEM (n=4–6). Of compounds tested thus far, the $NH_2$-substituted derivative appeared to have greatest activity. Another $N^G$ substitution tested for inhibition of induced nitrite release had two methyl groups on one of the arginine guanidino nitrogens. Concentration-response relationships for inhibition of A23187-stimulated nitrite release by bovine aortic endothelial cells (BAEC) are shown in FIG. 9a for the N,N-disubstituted derivative in comparison with several monosubstituted derivatives. Nitrite production was measured as an indication of nitric oxide synthesis since nitric oxide spontaneously decays to nitrite. Nitrite production by BAEC in a 2-hr. period was assessed in an L-arginine-free medium alone or in the presence of the indicated concentration of arginine analogs. The points plotted represent means±S.E. of the percent inhibition of nitrite production observed in 3 individual BAEC culture wells. The key on FIG. 9a indicates the groups substituted on the guanidino nitrogens of L-arginine. Me,Me— indicates the disubstituted analog tested; note that this compound is approximately equipotent to L-$N^G$-methylarginine.

FIG. 9b compares concentration-response relationships for the same set of mono- and disubstituted arginine analogs as FIG. 9a, plus an additional dimethyl analog with the two methyl groups on different guanidino nitrogens. The test is for inhibition of ACh-induced vasorelaxation in isolated rabbit aortic rings. The points plotted represent means±S.E. of the maximum responses to ACh observed in the presence of the indicated concentrations of analogs (n=4). Note that the analog with two methyl groups on one guanidino nitrogen (Me,Me—) is an active inhibitor whereas the compound with one methyl group on each of the guanidino nitrogens (Me,Me'—) is not a good inhibitor.

Figure 11:
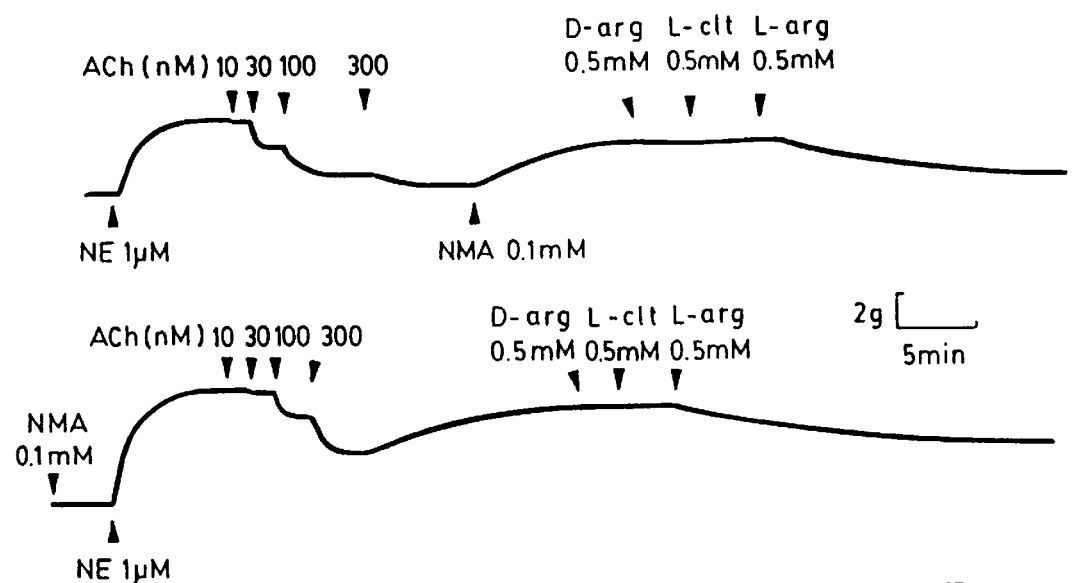
Figure 11:
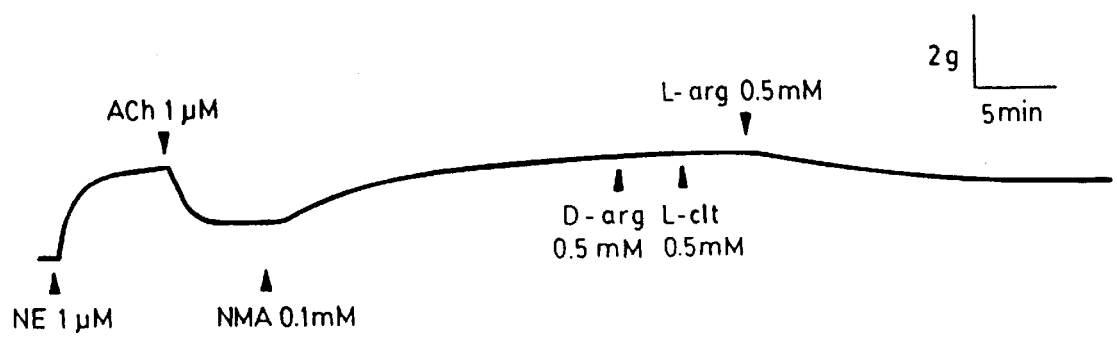

L-NMA was found to act as an arginine reversible inhibitor of EDRF/NO in vascular preparations from an array of species including guinea pig, rat, rabbit, dog and most notably human (see FIGS. 10 and 11). FIG. 10 shows inhibition of ACh-induced relaxation by NMMA in arteries from various vascular beds and species and the stereospecific reversal by L-arginine. Guinea pig pulmonary artery (GP PA), rat and rabbit aorta (Ao), and dog coronary (CA) and femoral artery (FA) were precontracted with NE (1 $\mu$M) and relaxed with a single concentration of ACh. Concentration of ACh: GP PA 1 $\mu$M, rat Ao 0.3 MM, rabbit Ao 0.3, dog CA 0.3 MM and dog PA 0.1 $\mu$M. The concentration of NMMA was 100 $\mu$M except for the rat Ao which was 5 $\mu$M. The concentrations of L-citrulline (L-cit), D-arginine (D-arg) and L-arginine (L-arg) were all 0.5 mM. Bars are mean values±SEM (n=4–6).

FIG. 11 contains representative physiograph tracings which depict ACh-induced relaxation of NE-preconstricted rings prepared from rabbit aorta (upper panel) and human internal mammary artery (lower panel). In both tissues, NMMA is shown to attenuate ACh-induced vasorelaxation; addition of excess L-arginine restores relaxation.

L-NMA also inhibits EDRF/NO release from bovine endothelial cells grown in culture (FIG. 12) and from the isolated guinea pig heart (FIG. 13) when challenged with an endothelium-dependent vasodilator.

FIG. 12 illustrates inhibition by NMMA of calcium ionophore stimulated nitrite release from bovine aortic endothelial cells grown in cell culture. Cells were stimulated to release NO by addition of 3 $\mu$g/ml of ionophore (A23187) to the culture medium, alone, and in the presence of various concentrations of NMMA. The cumulative release of nitrite (the stable oxidation product of NO) during a 4-hour incubation at 37' is depicted as a function of NMMA concentration. Points are mean values±SEM (n=3).

FIG. 13 depicts inhibition by NMMA of histamine-induced nitrite release from the isolated coronary perfused guinea pig heart and its restoration by L-arginine. Hearts were perfused at constant pressure (40 cm $H_2O$) with Krebs-Henseleit buffer containing the thromboxane A2 analog (U-46619, 86 nM) to induce coronary vasoconstriction. Histamine was administered as a rapid bolus injection into the aorta and net nitrite release during the subsequent 2.5 minutes was determined. Bars represent mean values±SEM (n=4–6). Not shown here is that histamine elicits a dose-dependent increase in coronary flow (vasodilation) which is attenuated by L-NMA, but restored by addition of excess L-arginine. Thus, it appears that NO synthesis from L-arginine mediates, at least in part, histamine-induced coronary artery vasodilation in the guinea pig heart.

Administration of L-NMA (1–10 mg/kg, intravenously) but not D-NMA to an anesthetized guinea pig elicits a sustained rise in diastolic BP due to inhibition of resting levels of EDRF/NO synthesis (FIGS. 14 and 15). A similar but more potent action was observed with L-$N^G$-aminoarginine (FIGS. 16 and 17). FIGS. 15 and 16 depict the time course of pressor effect elicited by NMMA (NMA; FIG. 15) and L-$N^G$-aminoarginine (NAA; FIG. 16) in the phenobarbital anesthetized guinea pig. Points are mean changes in diastolic arterial pressure (±SEM; n=4–5). Control systolic and diastolic BP was 75±3 and 51±3 mm Hg, respectively. Similarly L-$N^G$-ethylarginine (L-NEA) was tested in vivo and found also to cause a sustained pressor effect in the guinea pig.

A murine cancer cell line, EMT6, has been observed to release large quantities of nitrite into the culture medium when activated by bacterial ET, IFN and various cytokines. Thus EMT6 cytosolic preparations (i.e., cell-free solutions) were prepared and an enzyme activity was characterized which forms NO and citrulline from arginine. This reaction requires NADPH (FIG. 18 and 19) and other cofactors.

FIG. 18 shows the time course of nitrite production at 37' C by cytosolic preparations from EMT6 cells that were either untreated (control) or stimulated with IFN and endotoxin. Incubation mixtures were 100 $\mu$l total volume containing: 40 $\mu$l cytosol (100,000×g supernatant), 2 mM L-arginine, 2 mM NADPH, 20 mM TRIS (pH 8.0) and a "cocktail" of protease inhibitors. Nitrite synthesis is observed with cytosol prepared from stimulated cells but not from control cells.

From kinetic studies an apparent Michaelis-Menton constant for L-arginine utilization by the enzyme was deduced. FIG. 20 is a Lineweaver-Burke plot for synthesis of nitrite from L-arginine by cytosol from stimulated EMT6 cells. The rate of nitrite formation was evaluated over a range of L-arginine (ARG) concentrations (from 0.03–2.0 mM) under conditions similar to that described for FIG. 18, except that incubates contained 50 $\mu$l cytosol in a total volume of 80 $\mu$l. Open and filled circles represent results obtained with each of two cytosol preparations. From these results an apparent Km value of 61.6 $\mu$M can be extrapolated for the utilization of ARG by the enzyme pathway which forms NO. $N^G$-substituted arginine analogs were screened for precise quantitation of their ability to inhibit arginine-dependent NO formation by the EMT6 enzyme system. Thus, from data such as that presented in FIG. 21 it can be calculated that NMMA is a competitive inhibitor of arginine utilization with an apparent Ki of 5–10 $\mu$M. The ethyl-substituted compound is approximately 10-fold less active in this assay (FIG. 22).

It was concluded from these studies that NO synthesis from L-arginine is demonstrable in a wide variety of in vitro preparations, from an array of species. NO is an important mediator of vasodilation in vivo and probably plays an important role in vascular homeostasis. Finally, $N^G$-substituted arginine analogs may be used as specific blockers of the enzymatic pathway for NO generation. Thus, this class of arginine antagonists may offer specific relief from hypotension resulting from conditions which cause excess NO generation, such as those indicated in Examples 1 and 2.

EXAMPLE 4

Septic shock, a life-threatening complication of bacterial infections, affects 150,000 to 300,000 patients annually in the United States (Parrillo, J. E., 1989, Septic Shock in Humans: Clinical Evaluation, Pathogenesis, and Therapeutic Approach. In Textbook of Critical Care, 2nd edition. Shoemaker, et al., editors, Saunders Publishing Co., Philadelphia, Pa., pp. 1006). The cardiovascular collapse and multiple metabolic derangements associates with septic shock are due largely to bacterial ET, which has been shown to elicit a septic shock-like condition when administered to animals (Natanson, et al., 1989, Endotoxin and Tumor Necrosis Factor Challenges in Dogs Simulate the Cardiovascular Profile of Human Septic Shock. J. Exp. Med. 169:823). ET is known to stimulate the synthesis and release of several cytokines and biological mediators having hypotensive activity; among the factors released, TNF, PAF, prostacyclin and complement-derived C5a anaphylatoxin have been proposed as important contributors to the cardiovascular collapse of septic shock (Hesse, et al., 1988, Cytokine Appearance in Human Endotoxemia and Primate Bacteremia, Surg. Gynecol. Obstet. 166:147; Etienne, et al., 1986, The Relative Role of PAF-acether and Icosanoids in Septic Shock, Pharmacol. Res. Commun. 18:71; Halushka, et al., 1985, Elevated plasma 6-keto-prostaglandin F1 alpha in Patients in Septic Shock, Crit. Care Med. 13:451; Smedegard, et al., 1989, Endotoxin-induced Shock in the Rat: A Role for C5a, Am. J.Pathol. 135:489). Although it has been shown that animals pretreated with anti-TNF antibodies (Beutler et al., Passive immunization against cachectin/ TNF protects mice from lethal effects of ET, Science, 229:869), PAF receptor antagonists (Casals-Stenzel, 1987, Protective Effect of WEB 2086, a Novel Antagonist of Platelet Activating Factor in Endotoxin Shock, European J. Pharmacology 135:117), and prostacyclin synthesis inhibitors (Wise, et al., 1985, Ibuprofen, Methylprednisolone, and Gentamycin as Cojoint Therapy in Septic Shock, Circ. Shock 17:59) are significantly protected against septic shock, the relative importance of these mediators in the pathology of septic shock is presently uncertain. There is also evidence that some of these mediators may act indirectly via release of secondary mediators. Thus, the finding that anti-TNF antibodies have little or no protective effect when given after ET exposure (Beutler, et al., 1985, Passive immunization against cachectin/tumor necrosis factor protects mice from lethal effects of endotoxin. Science, 229:869) suggests that TNF stimulates the production of another factor that is the actual hypotensive agent; once initiated, synthesis and release of that factor can apparently continue even in the absence of detectable TNF levels.

The present inventors have shown that nitrite accumulates when cultured mouse endothelial cells are exposed to immunomodulators and endotoxin (Kilbourn, et al., 1990, Endothelial cell production of nitrogen oxides in response to interferon gamma in combination with tumor necrosis factor, interleukin-1, or endotoxin. J. Natl. Cancer Inst. 82:722). That this nitrite arises from the nitric oxide (NO) synthetic pathway is indicated by the observation that its accumulation is L-arginine-dependent and blocked by $N^G$methyl-L-arginine (L-NMA), a selective inhibitor of NO synthase (Hibbs, et al., 1988, Macrophage Cytotoxicity: Role for L-Arginine Deiminase and imino Nitrogen Oxidation to Nitrite. Biochem. Biophys. Res. Commun. 157:87). Since NO is a potent endothelium-derived relaxing factor (EDRF), these studies suggested that overprotection of NO might account for the cardiovascular changes associated with endotoxin and cytokine administration. Consistent with this view, the present inventors have found that the hypotensive response elicited by TNF in dogs can be completely reversed by administration of L-NMA (Kilbourn, et al., 1990, $N^G$methyl-L-arginine inhibits tumor necrosis factor induced hypotension: implications for the involvement of nitric oxide. Proc. Natl. Acad. Sci., U.S.A. 87:3629). In the present study the effect of L-NMA on endotoxin-induced shock in dogs was examined. The present findings indicate that NO is an important mediator of endotoxin-induced hypotension and that inhibitors of NO synthesis should be of value in the treatment of septic shock.

Reagents: $N^G$-Methyl-L-arginine was synthesized as previously described (Corbin, et al., 1974, $N^G$-Methylated Arginines: Convenient Preparation of $N^G$-Methylarginines. Anal. Biochem. 57, 310–312) and purified by crystallization as the monoflavianate salt. A solution of the free amino acid was obtained by stirring a suspension of the salt with Dowex-1 (OH); after neutralization with HCl, the concentration of L-NMA was determined by amino acid analysis using the crystalline monoflavianate salt as standard. Endotoxin (*Escherichia Coli;* B0128:B12) and all other reagents were purchased from Sigma Chemical Company, St. Louis, Mo. Nitroglycerin was purchased from DuPont Pharmaceuticals, Wilmington, Del.

Animals: Studies were carried out on 12 conditioned mongrel dogs (9 males and 3 females) weighing 22–32 kg (avg=25.3 kg). Animal care was in accordance with the recommendations of the American Association for Accreditation of Laboratory Animal Care, and met all standards prescribed by the Guide for the Care and Use of Laboratory Animals (Guide for the Care and Use of Laboratory Animals (1978) Dept. of Health, Education and Welfare, Washington, D.C. (Publ. No. 78-23). Animal protocols were approved by The University of Texas Animal Welfare Committee. The dogs were fasted overnight prior to the day of experimentation. They were anesthetized with sodium pentobarbital (25 mg/kg I.v.). Dogs were then endotracheally intubated and ventilated with a piston-driven respirator (Harvard instruments) using room air at a tidal volume of 20 ml/kg and at a rate of 10 to 12 breaths per minute, adjusted to achieve a normal arterial pH and $pCO_2$ (Instrumentation Laboratories 1L13012 pH/Blood Gas Analyzer). Catheters were placed percutaneously into the femoral and pulmonary arteries; In the latter, a flow-directed thermal-dilation catheter was used (Abbott Critical Care Systems).

Physiologic measurements: Mean SAP and heart rate were continuously monitored (Parametron 7048 Monitoring System, Roche) and stored on a magnetic disk using an analog-to-digital converter (Scientific Solutions, Inc.). Cardiac output (CO) was determined as the mean of six measurements by thermal-dilution. Systemic vascular resistance was calculated as (SAP X80)/CO and expressed as dynes-sec/$cm^2$.

Protocol: After the blood pressure and heart rate stabilized, endotoxin (40 ug/kg, in 10 ml of phosphate-buffered saline (PBS), pH 7.4) was infused i.v. over 2 minutes. This dose of endotoxin typically induces severe and often lethal cardiovascular collapse in the dog. Blood pressure was monitored, and when either SAP fell below 60 mmHg or a stable nadir in systemic arterial pressure (SAP) was maintained for 10 minutes, L-NMA was administered (20 mg/kg in 5 ml of PBS i.v. over 1 min.). In most experiments, L-arginine (400 mg/kg in 20 mi PBS) was administered ten minutes later by i.v. infusion over 2 minutes. In control experiments, dogs without prior exposure to endotoxin received L-NMA alone. To simulate the hypotension observed in dogs receiving endotoxin, one group of dogs received a continuous i.v. infusion of nitroglycerin (2 mg/ml) at a rate adjusted to maintain the SAP at 60–70 mm Hg. Nitroglycerin-treated dogs then received L-NMA (20 mg/kg) and 20 minutes later L-arginine was administered (400 mg/ml).

Statistics: Statistical significance was evaluated using Student's test and either a one-tailed or two-tailed analysis as appropriate for comparisons.

A representative blood pressure tracing which depicts the effect of endotoxin on systemic arterial pressure in the anesthetized dog is shown in FIG. 23. Cardiovascular parameters for this and 3 additional dogs are summarized in Table 1 (Study 1).

TABLE 1

Hemodynamic Effects of L-NMA during Hypotension

| Type of Evaluation | Systemic Arterial Pressure (mHg) | Heart Rate (beats/min) | Cardiac Output (L/min) (dynes-sec/cm$^5$) | Systemic Vascular Resistance |
|---|---|---|---|---|
| Study 1: Endotoxin-treated (n = 4) | | | | |
| Baseline | 128.3 ± 9.4 | 119.5 ± 6.0 | 2.99 ± 0.32 | 3564 ± 454 |
| After Endotoxin | 59.5 ± 3.1** | 124.0 ± 7.6 | 2.17 ± 0.44 | 2403 ± 352 |
| After L-NMA | 107.3 ± 9.6** | 123.3 ± 4.8 | 2.03 ± 0.32 | 4462 ± 552** |
| After L-Arginine | 52.7 ± 8.8** | 116.7 ± 18.8 | 2.31 ± 0.43 | 1851 ± 171* |
| Study 2: Nitroglycerin-treated (n = 3) | | | | |
| Baseline | 128.3 ± 10.2 | 143.7 ± 12.1 | 3.14 ± 0.21 | 3294 ± 74 |
| During Nitroglycerin | 64.7 ± 2.7** | 137.3 ± 5.0 | 2.72 ± 0.27 | 1924 ± 132** |
| After L-NMA | 81.8 ± 3.5* | 191.7 ± 35.0 | 3.85 ± 0.8 | 1851 ± 399 |
| After L-Arginine | 56.9 ± 13.0 | 148.7 ± 19.9 | 5.15 ± 1.08 | 1088.2 ± 491 |

For study 1, dogs were anesthetized, instrumented, and baseline cardiovascular measurements were recorded (Pretreatment). Endotoxin (40 ug/kg) was then administered and cardiovascular parameters were monitored. When blood pressure either reached a stable nadir or declined below 60 mmHg (After endotoxin), L-NMA (20 mg/kg) was administered, and cardiovascular parameters were again determined (After L-NMA). After an additional ten min, L-arginine (400 mg/kg) was administered and cardiovascular measurements were determined 2 min. later (After L-Arginine). Results are reported as means ± S.E., (n = 4). Study 2 was carried out similarly, except that endotoxin was not administered. Instead, dogs received a continuous infusion of nitroglycerin (2 mg/ml) titrated to maintain SAP AT 65 MM hG, (N = 3). Asterisks indicate statistically significant difference (*p < 0.005, **p < 0.001) from the immediately proceeding condition.

ET (40 ug/kg) produced a marked decrease in blood pressure within 120 min. (ΔSAP=−69±6 mmHg, p<0.05). Untreated, this dose of endotoxin typically causes lethal cardiovascular collapse in the dog. L-NMA largely reversed the hypotension within 1.5 minutes, increasing SAP by 47.8±6.8 mm Hg (p<0.01) and SVR by 2060±338 dynes-sec/cm$^5$ (p<0.01); HR and CO were unchanged (Table 1). L-arginine reversed the effect of L-NMA and restored the endotoxin-induced hypotension, decreasing both SAP (p<0.0.01) and SVR (p<0.01) to values similar to those observed before administration of L-NMA. As illustrated in FIG. 23, after L-arginine, blood pressure decreased to levels lower than those observed prior to L-NMA administration, suggesting that the capacity to overproduce NO progressed during the period when NO production was blocked by L-NMA (p=NS). FIG. 23 shows the time course of changes in mean systemic arterial pressure (SAP) in a pentobarbital-anesthetized dog following the i.v. administration of endotoxin (ET), N$^G$methyl-L-arginine (L-NMA), and L-arginine (L-Arg). Data from this and additional experiments are summarized in Table 1 (above).

In view of the potential clinical use of NO-synthesis inhibitors in endotoxin- and cytokine-induced shock, it is important to establish that L-NMA can provide long-term reversal of hypotension. It was found that a single i.v. dose of L-NMA (20 mg/kg) restored normal blood pressure for 30–60 minutes. If an additional dose of L-NMA (20 mg/kg) was given when the blood pressure began to decrease again, normal blood pressure could be maintained for at least 2 hours in the endotoxin-treated dog. Results of a typical study are shown in FIG. 24. The maintenance of normal blood pressure continued to be dependent on L-NMA even after 2 hours since L-arginine could still restore endotoxic hypotension at this time (i.e., a decline in blood pressure <45 mm Hg). FIG. 24 shows the time course of changes in mean systemic arterial pressure (SAP) in a pentobarbital-anesthetized dog following the i.v. administration of endotoxin. After 53 min. blood pressure declined to 47 mm Hg (ASAP=−61 mm Hg). Administration of L-NMA (20 mg/kg) resulted in a rapid reversal of the severe hypotension (73 mm Hg increase in SAP within 10 min). Blood pressure was maintained for 48 min by the first dose of L-NMA then started to decline. A second dose of L-NMA restored the blood pressure to a level equivalent to the first dose and maintained the SAP greater than 100 mm Hg for 2 hrs. To demonstrate than the potential for hypotension was still remained, the effect of L-NMA was reversed with an excess of L-arginine (400 mg/ml). This resulted in a decline in blood pressure to 43 mm Hg (ASAP=−77 mm Hg).

As shown in Table 2, L-NMA alone had a significant but modest hypertensive effect in control dogs not treated with endotoxin; L-NMA increased SAP by only 24.8±2.7 mm Hg (p,0.01) with an associated increase in SVR (p,0.01), and decreases in heart rate (HR) and cardiac output (CO) that did not reach statistical significance. L-arginine (400 mg/kg) fully reversed the pressor effect of L-NMA.

TABLE 2

HEMODYNAMIC EFFECTS OF L-NMA IN CONTROL DOGS

| | Systemic Arterial Pressure (mmHg) | Heart Rate (beats/min) | Cardiac Output (L/min) | Systemic Vascular Resistance (dynes-sec/cm$^5$) |
|---|---|---|---|---|
| Baseline | 129.0 ± 10.9 | 121 ± 17.9 | 3.54 ± 0.68 | 3115 ± 347 |
| After L-NMA | 153.8 ± 11.4** | 82.5 ± 6.1 | 2.12 ± 0.26 | 5967 ± 523* |

Experiments were as described in FIG. 23, except that endotoxin was not administered. Results are reported as means ± S.E., (n = 4). Asterisks indicate significant differences from baseline (*p, 0.005, **p, 0.001). L-NMA = N$^G$-monomethyl-L-arginine.

In an additional series of experiments, blood pressure was reduced to 65 mm Hg by continuous i.v. infusion of nitroglycerin, a hypotensive agent that forms NO by an L-arginine and NO synthetase-independent mechanism.

Administration of L-NMA (20 mg/kg) to those dogs resulted in only a 17.1±5.0 mm Hg change without significant alteration in HR, CO, or SVR (Table 1, Study 2).

The pathogenesis of the cardiovascular collapse that -occurs during septic shock is poorly understood. Current treatment includes i.v. fluid administration and use of pressor drugs to increase peripheral vascular resistance and cardiac output. Very recently, endotoxin-binding agents including polymyxin B (Hanasawa, et al., 1989, New Approach to Endotoxic and Septic Shock by Means of Polymyxin B Immobilized Fiber Surg. *Gynecol. Obstet.* 168:232.) and antibodies which neutralize TNF (Tracey, et al., 1987, Anti-cachectin/TNF monoclonal antibodies prevent septic shock during lethal bacteremia *Nature* 330:662–664.) have been used in an attempt to modify the sequelae of septic shock. Although the latter approaches may have prophylactic value, there is not evidence that septic shock can be easily or rapidly reversed by removal of endotoxin or TNF. Therapy of patients already in septic shock requires intervention at secondary and tertiary steps in the cascade of events initiated by endotoxin. because the development of hypotension and other changes associated with septic shock may depend on complex interactions between cytokines, eicosanoids, PAF, activated complement components, and other factors, it is not surprising that several interventions have been found to be at least partially effective in some models. Inhibitors of prostaglandin synthesis and PAF receptor antagonists are two major classes of compounds that may have therapeutic potential (8–9). Although these agents appear to be effective, they have been tested primarily in animals administered very large doses of endotoxin (e.g., 1 to 40 mg/kg, or about 1000 times larger than the dose used here). The onset of hypotension occurs within a few minutes in such animals and may not accurately reflect the cytokine-mediated processes characteristic of clinical septic shock. In the present study with endotoxin and in previous clinical septic shock, in the present study with endotoxin and in a previous study with TNF (Kilbourn, et al. 1990, $N^G$-methyl-L-arginine inhibits tumor necrosis factor induced hypotension: Implications for the Involvement of Nitric Oxide, *Proc. Natl. Acad. Sci.*, U.S.A. 87:3629.), microgram doses of ET or TNF were administered, and the hypotensive response occurred after a delay of 30 to 90 min.

The present inventors demonstration (Kilbourn, et al. 1990, $N^G$-methyl-L-arginine inhibits tumor necrosis factor induced hypotension: implications for the involvement of NO, *Proc. Natl. Acad. Sci.*, U.S.A. 87:3629.) that dogs given TNF exhibit a severe hypotension that can be substantially reversed by administration of L-NMA suggested that overproduction of NO is a major factor in TNF-induced shock. The data in Table 1 show that L-NMA has a rapid and strong anti-hypotensive effect in the endotoxemic dog.

The effects of L-NMA on cardiac output and SVR in the four control dogs showed considerable variation. In two dogs, cardiac output decreased markedly (Δ>b 1.5L/min.) and calculated SVR increased dramatically (Δ≧3500 dynes-sec./cm$^5$). In contrast, major changes in cardiac output after L-NMA administration were not seen in any of the ET-treated dogs or in the other two control dogs; in the latter, SVR increased by only about 1400 dynes-sec./cm$^5$. Although these results suggest the possibility that L-NMA may have a direct effect on cardiac output under control conditions, additional studies are required. It is likely that activation of the arterial baroreceptor reflex mechanism (Lodato, Control of Cardiac Output, In: Dantzer, D. R. (ed. Cardiopulmonary Critical Care, W. B. Saunders, Philadelphia, Pa. (in press).) accounts for the L-NMA-induced decrease in HR and CO under control conditions. In support of this view, it was observed that control dogs given phenylephrine at a dose that elevated SAP to a level similar to that produced by L-NMA alone also showed similar decreases in HR and CO. The lack of effect of L-NMA on HR or CO in hypotensive dogs may be because the level of hypotension was below the range of baroreceptor reflex sensitivity (Lodato, Control of Cardiac Output, In: Dantzer, D. R. (ed.) Cardiopulmonary Critical Care, W. B. Saunders, Philadelphia, Pa. (in press).)

In view of the multiple mediators reported to contribute to septic shock, it was the expectation that even complete inhibition of NO formation could not fully reverse the hypotension of ET-induced shock. Indeed, that blood pressure was not fully restored to pretreatment values by 20 mg/kg L-NMA suggests that mediators other than NO contribute modestly to hypotension in the endotoxemic dog. The possibility that NO synthesis was not fully inhibited by the administered dose of L-NMA provides an alternative explanation for the failure to fully restore blood pressure to pretreatment levels. Although direct determination of the extent of NO synthesis inhibition is not possible in vivo, limited dose response studies indicate that L-NMA doses greater than 20 mg/kg do not have a significantly greater pressor effect. The ET-induced hypotension escaping blockade by 20 mg/kg L-NMA may be due to mediators other than NO. While it may be that long-term inhibition by L-NMA may be self-limited by conversion to L-Arginine (Salvemini, et al., 1990, Immediate Release of a Nitric Oxide-Like Factor from Bovine Aortic Endothelial Cells by *Escherichia coli* Lipopolysaccharide. *Proc. Natl. Acad. Sci.* 87:2593.), such metabolism would not be expected to diminish the short-term pressor effect of L-NMA which is shown in FIG. 23. Nevertheless, the finding that L-NMA restores blood pressure to normal or near normal values indicates that overproduction of NO is a major, and perhaps the major, cause of hypotension in endotoxic shock.

In one experiment, a single injection of L-NMA (20 mg/kg) was able to reverse endotoxin-elicited hypotension for 30 to 60 min. As shown in FIG. 24, normotension could be maintained for at least 2 hours by a subsequent dose of L-NMA. The long-term reversal of endotoxin-induced hypotension with L-NMA demonstrates the potential clinical utility of this agent. In conclusion, these results suggest that NO synthesis inhibitors should be of considerable value in the treatment of septic shock.

EXAMPLE 5

Administration of ET to dogs was clearly more toxic and less predictable than TNF administration. In this experimental series, with small doses of ET (1 μg/kg), blood pressure was observed to decline within 60–90 minutes. After the nadir of the blood pressure was reached, NMMA (5 mg/kg) was administered. Within 1.5 minutes the blood pressure increased by 33±2.5 mmHg. This increase in blood pressure was reversed by the subsequent administration of L-arginine (100 mg/kg) and the blood pressure was observed to fall precipitously below the pre-NMMA level. Administration of NMMA to endotoxemic dogs resulted in a significantly greater increase in blood pressure when compared to untreated animals (33 mm Hg versus 12 mm Hg). To demonstrate if lethal endotoxin-induced shock could be reversed by NMMA, endotoxin-induced shock could be reversed with NMMA, endotoxemic dogs that had received 100 μg/ml of endotoxin were treated with 20 mg/kg NMMA (FIG. 23). This resulted in a remarkable 65 mm increase in blood pressure compared to a 35 mm increase in a normal untreated dog. Furthermore, blood pressure could be maintained with readministration of NMMA (FIG. 24).

Since NMMA specifically blocks NO synthesis, these observations suggest a role for NO in immunomodulator-induced shock and in septic shock. Since the administration of L-arginine overcomes the competitive inhibition affected by L-NMMA by providing an excess of the required precursor for NO synthesis, this work also suggests a role for arginine in the generation of hypotension associated with these two processes. The reversal of hypotension by NMMA appears to be selective for TNF and ET-induced hypotension since reduction in the blood pressure to a similar level of hypotension with nitroglycerin was not antagonized by NMMA administration. This provides further support for a role of NO in these processes since hypotension was not antagonized by NMMA when induced by an agent that acts by an arginine-independent pathway.

The response of the dog to TNF and ET is similar to that observed in humans. In clinical trials in which TNF was administered to cancer patients, hypotension is the dose-limiting toxicity which restricts the dose of TNF which can be administered. As observed in the patient, the time of onset and severity of hypotension is variable in the dog. The administration of ET to the dog is associated with a more severe and uncontrollable form of hypotension than a bolus injection of TNF. This may be due to the fact that TNF has a short half-life in circulation (5 minutes), however, it is continually produced by endogenous sources after administration of ET. This may lead to an increased inductive drive to produce larger amounts of NO in response to ET as compared to TNF. This hypothesis is confirmed by the fact that lower doses of NMMA were required to reverse TNF-induced shock as compared to ET-induced shock.

NMMA does not inhibit the anti-tumor activity of TNF and IL-2, in vitro. TNF bioactivity was measured by the cytotoxicity towards murine L929 cells, in vitro. Addition of NMMA or $N^G$aminoarginine did not alter the cytolytic effect of TNF towards tumor cells in vitro (Table 3).

TABLE 3

Effects of NMMA on the Cytolytic Activity of rh-TNF
Against Actinomycin D-Treated L929 Cells

| [NMMA] (mM) | TNF Activity (Units/ml) |
|---|---|
| 0 | 594.5 |
| 0.125 | 536.9 |
| 0.250 | 538.2 |
| 0.500 | 562.4 |
| 0.750 | 404.7 |
| 1.0 | 415.7 |

Similarly, NMMA did not alter either the proliferation phase (data not shown) or the lytic phase of human LAK cells exposed to IL-2, in vitro (Table 4).

TABLE 4

Effects of NMMA on IL-2 Mediated Lymphokine
Activated Killer Cell Activity in vitro

| [NMMA] (mM) | % Target Cell Lysis* |
|---|---|
| 0 | 66.1 ± 9.5 |
| 0.25 | 63.3 ± 11.8 |
| 0.5 | 67.7 ± 10.8 |

TABLE 4-continued

Effects of NMMA on IL-2 Mediated Lymphokine
Activated Killer Cell Activity in vitro

| [NMMA] (mM) | % Target Cell Lysis* |
|---|---|
| 1.0 | 59.3 ± 7.5 |
| 2.0 | 75.1 ± 4.1 |

*% Lysis calculated from the % of release of radioactivity from $^{51}$Cr-labeled Raji Target cells minus spontaneous release. Effector cells were human blood lymphocytes cultured for 4 days in the presence of 40 U/ml of IL-2 (E:T = 80:1).

Aminoarginine is the most potent inhibitor of nitric oxide production measured thusfar. Since NMMA is metabolized to citrulline which can subsequently serve as a precursor for arginine biosynthesis, other arginine analogs were tested for their ability to inhibit nitric oxide production (Table 5).

TABLE 5

Comparison of the $ED_{50\%}$* values of
$N^G$-Substituted Arginine Analogs

| Analog | $ED_{50\%}$ |
|---|---|
| NMMA | 336.7 |
| Aminoarginine | 109.5 |
| Nitro-L-Arginine | 2115 |
| Nitro-D-Arginine | >4500 |
| Nitro-L-Arginine benzyl ester | >1200 |
| Nitro-L-Arginine methyl ester | 1826 |
| Nitro-D-Arginine methyl ester | >4500 |

*$ED_{50\%}$ + The effective dose of drug that inhibited 50% of the nitrite production by murine endothelial cells exposed to Gamma-Interferon (100 U/ml) and TNF (500 U/ml) in vitro.

The most potent derivative tested was $N^G$-aminoarginine. Subsequent testing in vivo, showed that aminoarginine was more effective than NMMA in reversing the hypotension associated with TNF administration in the dog (FIG. 25).

The reversal of ET shock (lethal dose) by $N^G$-aminoarginine (NAA) for 4 hrs. 38 min. was demonstrated using multiple doses of aminoarginine (NAA). FIG. 26 depicts systemic arterial pressure (SAP) versus time (min). ET (2 mg/kg), a lethal dose, was infused over 60 min. and NAA administered at 97, 165, and 374 min. to maintain blood pressure. The animal was survived for 24 hours and then autopsied. No pathological changes were observed in liver, lungs, heart, brain, bowel or kidney.

FIG. 27 demonstrates the ability of $N^G$-aminoarginine to reverse systemic hypotension mediated by interleukin-1. Subsequent administration of L-arginine obviated this reversal.

Changes may be made in the arginine antagonists and analogs or method steps of the invention without departing from the scope and spirit of the following claims.

What is claimed is:

1. A method for treating toxicity in a patient caused by excess levels of nitric oxide, the method comprising administering a therapeutically effective amount of a nitric oxide synthesis inhibitor to said patient.

2. The method of claim 1 where the toxicity is septic shock.

3. A method for the treatment of septic shock in a patient caused by excess levels of nitric oxide, the method comprising administering a therapeutically effective amount of a nitric oxide synthesis inhibitor to said patient.

4. A method for the inhibition of nitric oxide production in a patient having septic shock, the method comprising administering a therapeutically effective amount of a nitric oxide synthesis inhibitor to said patient.

5. A method for treatment of systemic hypotension in a patient having septic shock, caused by excess nitric oxide production comprising administering a therapeutically effective amount of a nitric oxide synthesis inhibitor to said patient.

6. The method of claim 5 where the nitric oxide production is induced by a cytokine.

7. A method for treatment of a patient having systemic hypotension induced by chemotherapeutic treatment with a cytokine comprising administering a therapeutically effective amount of a nitric oxide synthesis inhibitor.

8. The method of claim 6 or 7 where the cytokine is at least one of gamma interferon, interleukin-1, and interleukin-2.

9. The method of claim 6 or 7 where the cytokine is tumor necrosis factor.

10. A method for the treatment of a patient having systemic hypotension induced by endotoxin comprising administering a therapeutically effective amount of a nitric oxide synthesis inhibitor.

11. A method for prophylaxis or treatment of systemic hypotension in a patient caused by nitric oxide production induced by at least one cytokine selected from the group consisting of gamma interferon, interleukin-1, and interleukin-2 comprising administering an amount of a nitric oxide synthesis inhibitor sufficient to elevate blood pressure.

12. A method for prophylaxis or treatment of systemic hypotension in a patient caused by nitric oxide production induced by tumor necrosis factor comprising administering an amount of a nitric oxide synthesis inhibitor sufficient to elevate blood pressure.

13. The method of claim 1, 2, 3, 4, 5, 6, 7, 10, 11 or 12 where the nitric oxide synthesis inhibitor is an arginine analog.

14. The method of claim 1, 2, 3, 4, 5, 6, 7, 10, 11 or 12 where the nitric oxide synthesis inhibitor is nitro-L-arginine methyl ester.

15. The method of claim 1, 2, 3, 4, 5, 6, 7, 10, 11 or 12 where the nitric oxide synthesis inhibitor is a competitive inhibitor of nitric oxide synthase.

16. The method of claim 1, 2, 3, 4, 5, 6, 7, 10, 11 or 12 where the nitric oxide synthesis inhibitor is an $N^G$ substituted arginine or an $N^G,N^G$-disubstituted arginine.

17. The method of claim 16 wherein the $N^G$-substituted or $N^G$,N-disubstituted arginine has a nitro, amino, lower alkyl, lower hydroxyalkyl, carboxyalkyl, aminoalkyl or alkenyl substituent replacing a hydrogen of a guanidino amino group.

18. The method of claim 16 wherein the $N^G$-substituted arginine is $N^G$-arginine is $N^G$-nitroarginine, $N^G$methylarginine, $N^G$-ethylarginine or $N^G$-propylarginine.

19. The method of claim 16 wherein the $N^G$-substituted arginine is $N^G$-methyl-L-arginine.

20. The method of claim 1, 2, 3, 4, 5, 6, 7, 10, 11 or 12 wherein said therapeutically effective amount of a nitric oxide synthesis inhibitor inhibits production of nitric oxide from arginine.

21. The method of claim 20 where the therapeutically effective amount is from 0.1 to 100 mg/kg body weight.

22. The method of claim 1, 2, 3, 4, 5, 6, 7, 10, 11 or 12 wherein the administering is intravascular.

23. The method of claim 1, 2, 3, 4, 5, 6, 7, 10, 11 or 12 wherein the administering is parenteral.

24. The method of claim 1, 2, 3, 4, 5, 6, 7, 10, 11 or 12 wherein the administering is enteral.

25. The method of claim 1, 2, 3, 4, 5, 6, 7, 10, 11 or 12 wherein the administering is intraperitoneal, intramuscular, intradermal or topical.

* * * * *

UNITED STATES PATENT AND TRADEMARK OFFICE
CERTIFICATE OF CORRECTION

PATENT NO. : 5,770,623
DATED : June 23, 1998
INVENTOR(S) : Kilbourn, et. al.

It is certified that error appears in the above-identified patent and that said Letters Patent is hereby corrected as shown below:

Title page, item [63], insert --which is a continuation-in-part of PCT/US90/05199, Sept. 13, 1990--.

Column 22, line 16, in claim 18, delete "-arginine is" and insert -- Aminoarginine,--.

Signed and Sealed this

Seventeenth Day of November, 1998

Attest:

BRUCE LEHMAN

Attesting Officer    Commissioner of Patents and Trademarks